(12) United States Patent
Tippett et al.

(10) Patent No.: US 10,987,237 B2
(45) Date of Patent: Apr. 27, 2021

(54) ENDOVASCULAR PROSTHESIS AND DELIVERY DEVICE

(71) Applicant: Evasc Neurovascular Limited Partnership, Vancouver (CA)

(72) Inventors: Jonathan G. Tippett, Vancouver (CA); Eric Soun-Sang Fung, Vancouver (CA); Thomas R. Marotta, Etobicoke (CA); Ian T. B. Mcdougall, Vancouver (CA); Ian M. Penn, Vancouver (CA); Donald R. Ricci, Vancouver (CA)

(73) Assignee: Evasc Neurovascular Enterprises ULC, Vancouver (CA)

( * ) Notice: Subject to any disclaimer, the term of this patent is extended or adjusted under 35 U.S.C. 154(b) by 0 days.

(21) Appl. No.: 14/711,061

(22) Filed: May 13, 2015

(65) Prior Publication Data
US 2015/0342762 A1    Dec. 3, 2015

Related U.S. Application Data

(63) Continuation of application No. 14/065,788, filed on Oct. 29, 2013, now Pat. No. 9,056,024, which is a
(Continued)

(51) Int. Cl.
*A61F 2/89*   (2013.01)
*A61F 2/92*   (2013.01)
(Continued)

(52) U.S. Cl.
CPC ............... *A61F 2/89* (2013.01); *A61F 2/86* (2013.01); *A61F 2/91* (2013.01); *A61F 2/92* (2013.01);
(Continued)

(58) Field of Classification Search
CPC .................................. A61F 2/86; A61F 2/89
See application file for complete search history.

(56) References Cited

U.S. PATENT DOCUMENTS

| 5,354,309 | A | * | 10/1994 | Schnepp-Pesch | ......... A61F 2/82 606/198 |
| 5,954,765 | A | * | 9/1999 | Ruiz | ......................... A61F 2/92 606/194 |

(Continued)

FOREIGN PATENT DOCUMENTS

| CN | 1646069 A | 7/2005 |
| CN | 101247777 A | 8/2008 |

(Continued)

OTHER PUBLICATIONS

Office Action for Canadian Application No. 2,834,616 dated Oct. 24, 2014.
(Continued)

*Primary Examiner* — Christopher D. Prone
(74) *Attorney, Agent, or Firm* — Katten Muchin Rosenman LLP

(57) ABSTRACT

In one of its aspects, the present invention relates to an endovascular prosthesis. The endovascular prosthesis includes a first expandable portion expandable from a first, unexpanded state to a second, expanded state to urge the first expandable portion against a vascular lumen and a retractable leaf portion attached to the first expandable portion. The retractable leaf portion comprises at least one spine portion and a plurality of rib portions attached to the spine portion. Longitudinally adjacent pairs of rib portions are free of interconnecting struts. The endovascular prosthesis that can be unsheathed and re-sheathed for repositioning of the endovascular prosthesis prior to final deployment thereof. There is also described a delivery device that that is par-
(Continued)

ticularly well suited to delivering the present endovascular prosthesis through tortuous vasculature in the body.

23 Claims, 39 Drawing Sheets

Related U.S. Application Data continuation of application No. PCT/CA2012/000379, filed on Apr. 27, 2012.

(60) Provisional application No. 61/457,605, filed on Apr. 29, 2011, provisional application No. 61/457,604, filed on Apr. 29, 2011.

(51) Int. Cl.
*A61F 2/91* (2013.01)
*A61F 2/966* (2013.01)
*A61F 2/86* (2013.01)
*A61F 2/82* (2013.01)
*A61F 2/95* (2013.01)

(52) U.S. Cl.
CPC ........ *A61F 2/966* (2013.01); *A61F 2002/823* (2013.01); *A61F 2002/9511* (2013.01); *A61F 2002/9665* (2013.01); *A61F 2230/0006* (2013.01); *A61F 2230/0008* (2013.01); *A61F 2230/0023* (2013.01); *A61F 2250/0023* (2013.01); *A61F 2250/0029* (2013.01)

(56) References Cited

U.S. PATENT DOCUMENTS

| 6,248,566 | B1 | 6/2001 | Imanaka et al. |
| 6,273,908 | B1* | 8/2001 | Ndondo-Lay ........... A61F 2/885 606/194 |
| 6,673,100 | B2 | 1/2004 | Diaz et al. |
| 6,676,696 | B1 | 1/2004 | Marotta et al. |
| 6,997,944 | B2 | 2/2006 | Harrison et al. |
| 7,815,975 | B2 | 8/2010 | Pursley |
| 7,815,674 | B1 | 10/2010 | Ragazzo |
| 2002/0165605 | A1 | 11/2002 | Penn et al. |
| 2002/0173839 | A1 | 11/2002 | Leopold et al. |
| 2002/0188344 | A1 | 12/2002 | Bolea et al. |
| 2006/0004346 | A1 | 1/2006 | Begg |
| 2006/0116714 | A1 | 6/2006 | Sepetka et al. |
| 2007/0270903 | A1 | 11/2007 | Davis, III et al. |
| 2008/0281350 | A1 | 11/2008 | Sepetka et al. |
| 2009/0171439 | A1 | 7/2009 | Nissl |
| 2009/0177119 | A1 | 7/2009 | Heidner et al. |
| 2009/0216185 | A1 | 8/2009 | Gregorich et al. |
| 2010/0145308 | A1 | 6/2010 | Layman et al. |
| 2011/0245808 | A1 | 10/2011 | Voeller et al. |

FOREIGN PATENT DOCUMENTS

| CN | 101933855 A | 1/2011 |
| WO | 93/15775 A1 | 8/1993 |
| WO | 93/16479 A1 | 8/1993 |
| WO | 99/40873 A1 | 8/1999 |
| WO | 00/47134 A1 | 8/2000 |
| WO | 02/39924 A1 | 5/2002 |

OTHER PUBLICATIONS

Extended European Search Report for European Patent Application No. 12777587.2 dated Nov. 17, 2014.
International Search Report for International Application No. PCT/CA2012/000388 dated Aug. 9, 2012.
International Search Report for International Application No. PCT/CA2012/000379 dated Aug. 20, 2012.
Notification of the First Office Action for Chinese Patent Application No. 201280029588.2 dated May 19, 2015.
Notification of the First Office Action for Chinese Patent Application No. 201280029692.1 dated Jun. 3, 2015.

* cited by examiner

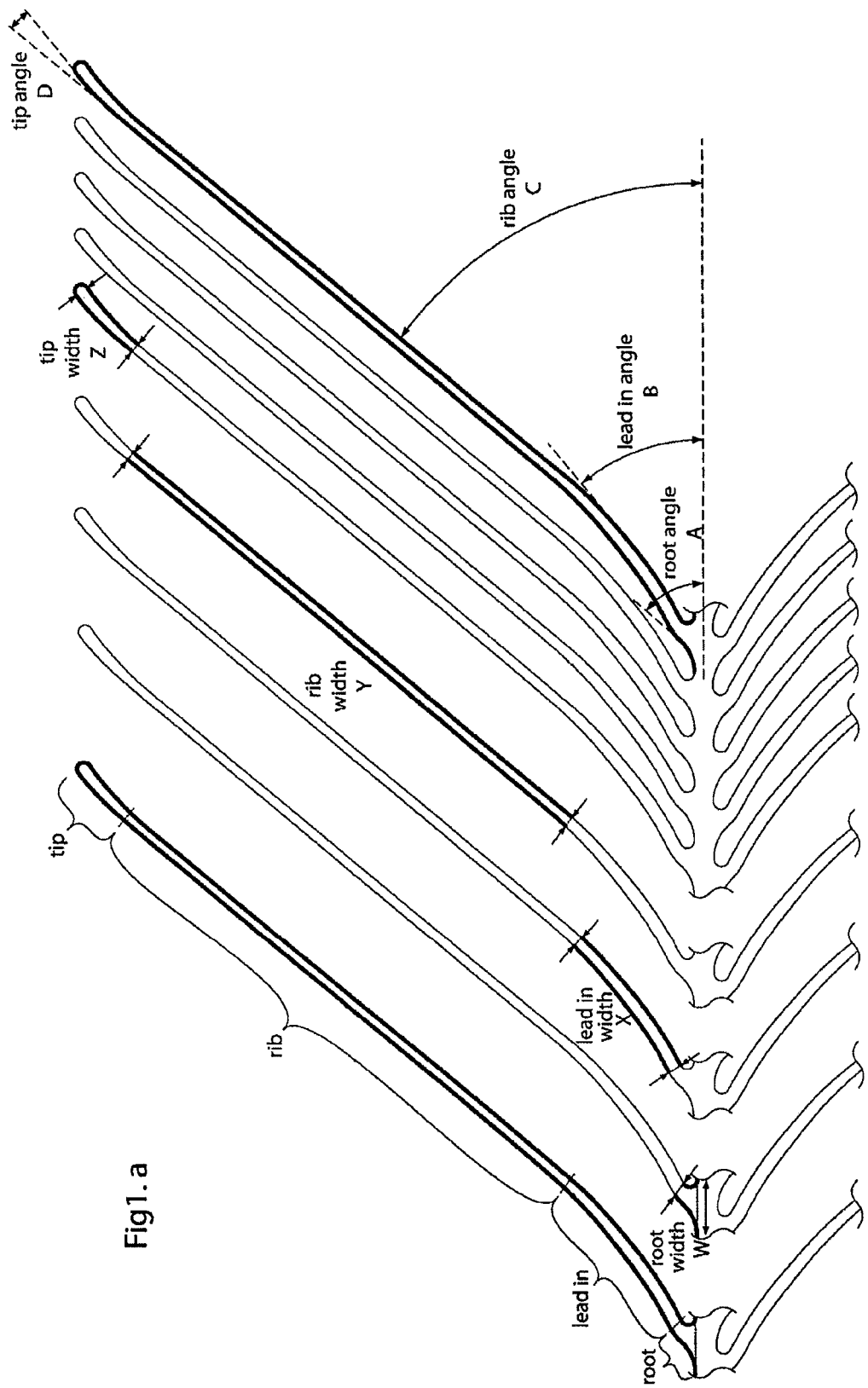
Fig1.a

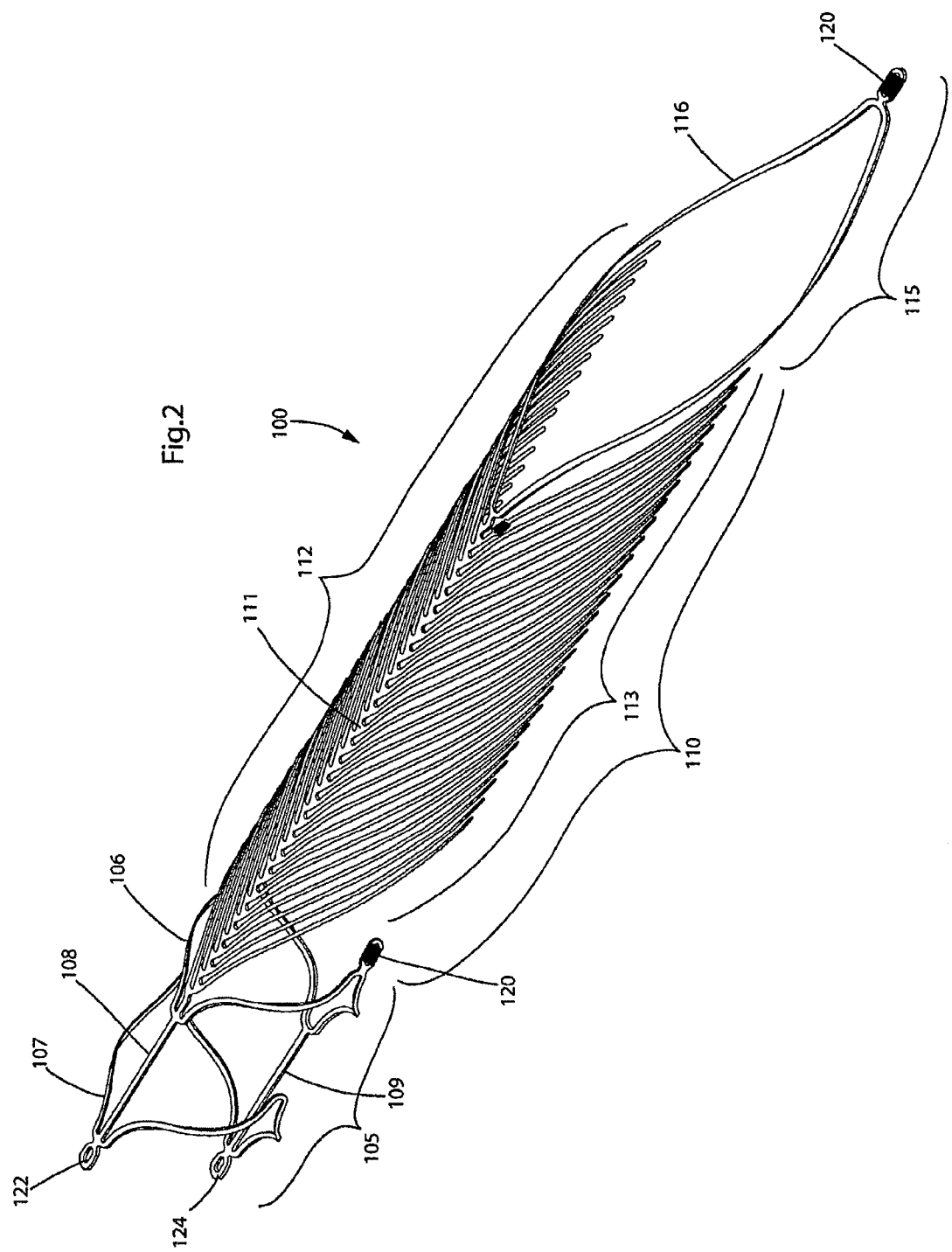

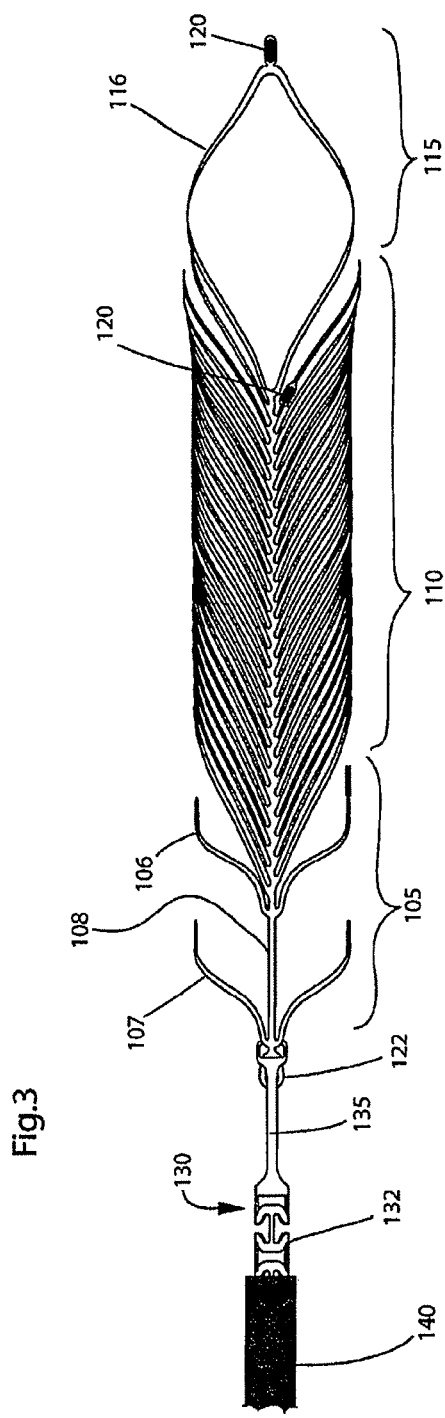

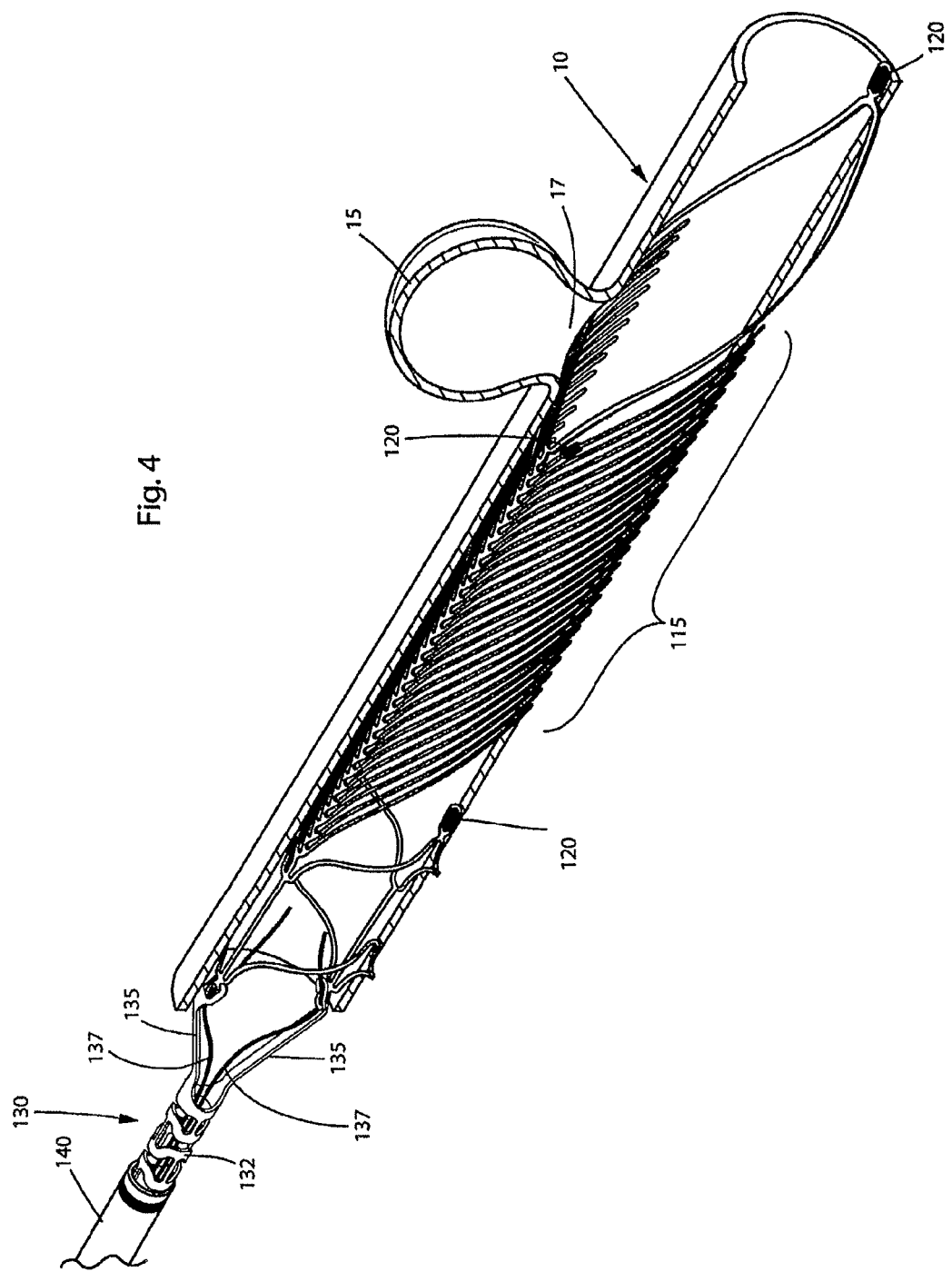

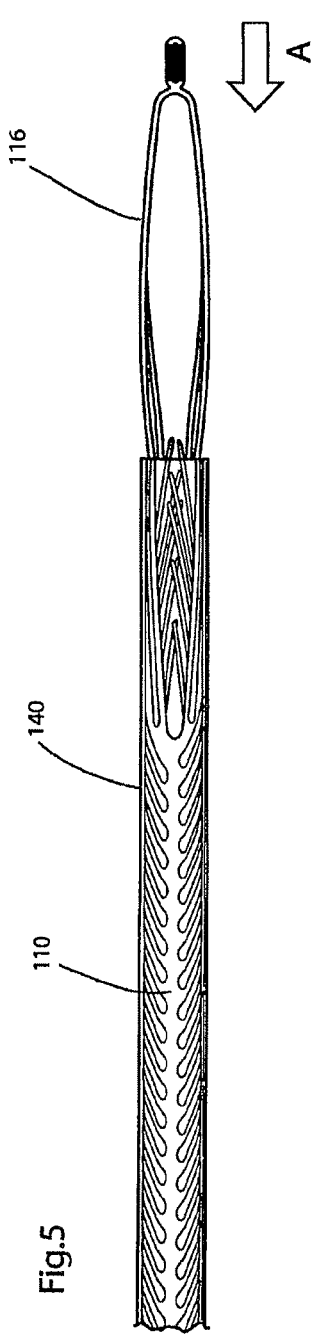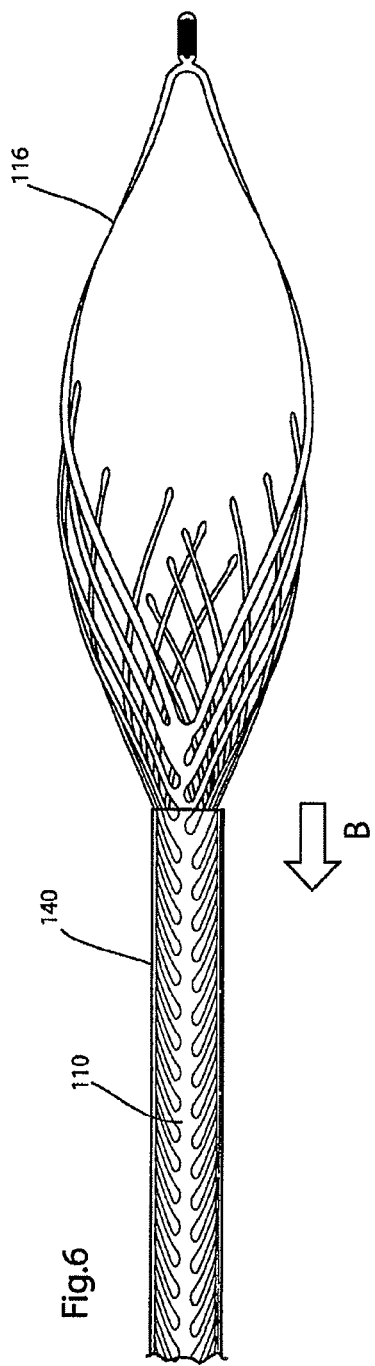

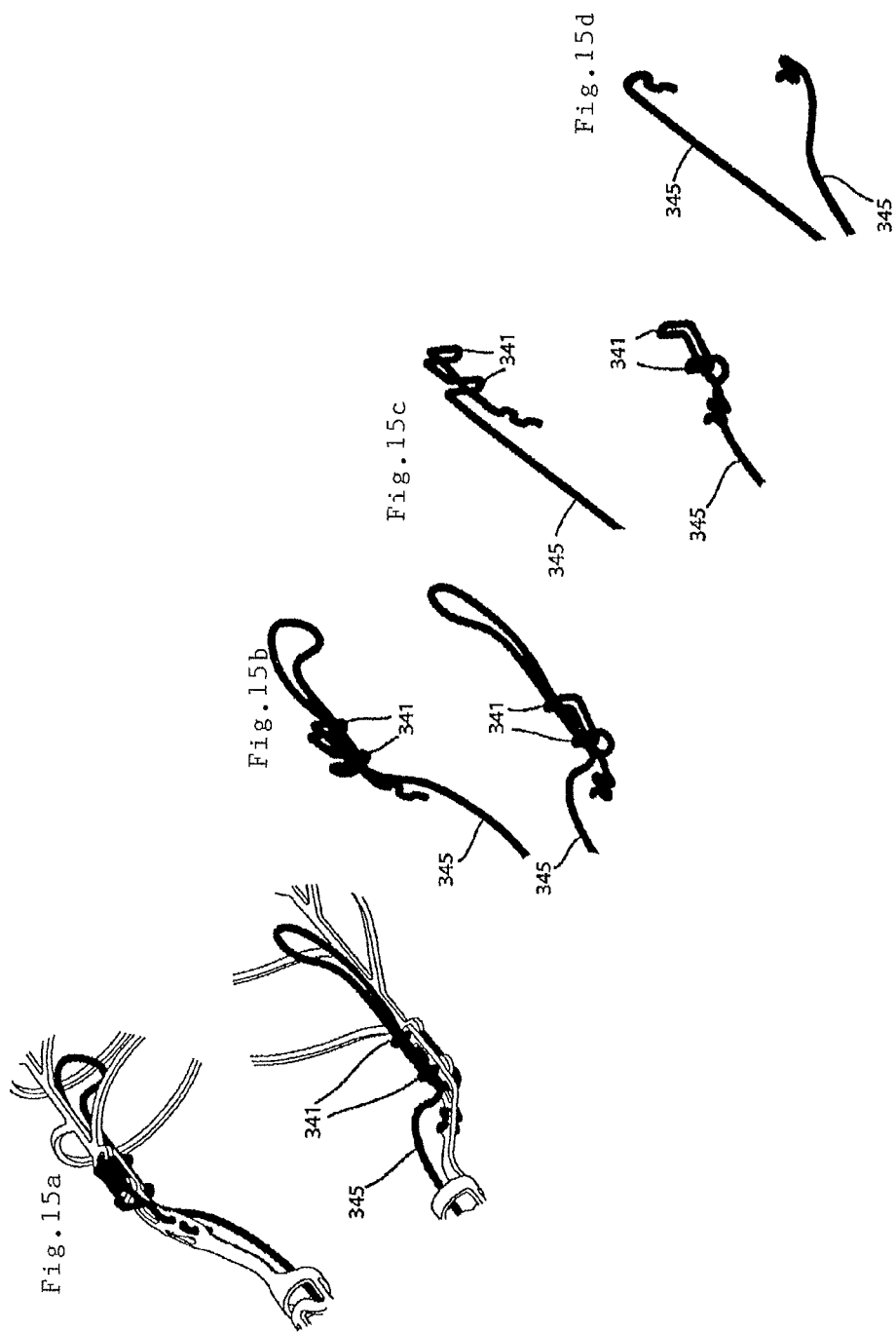

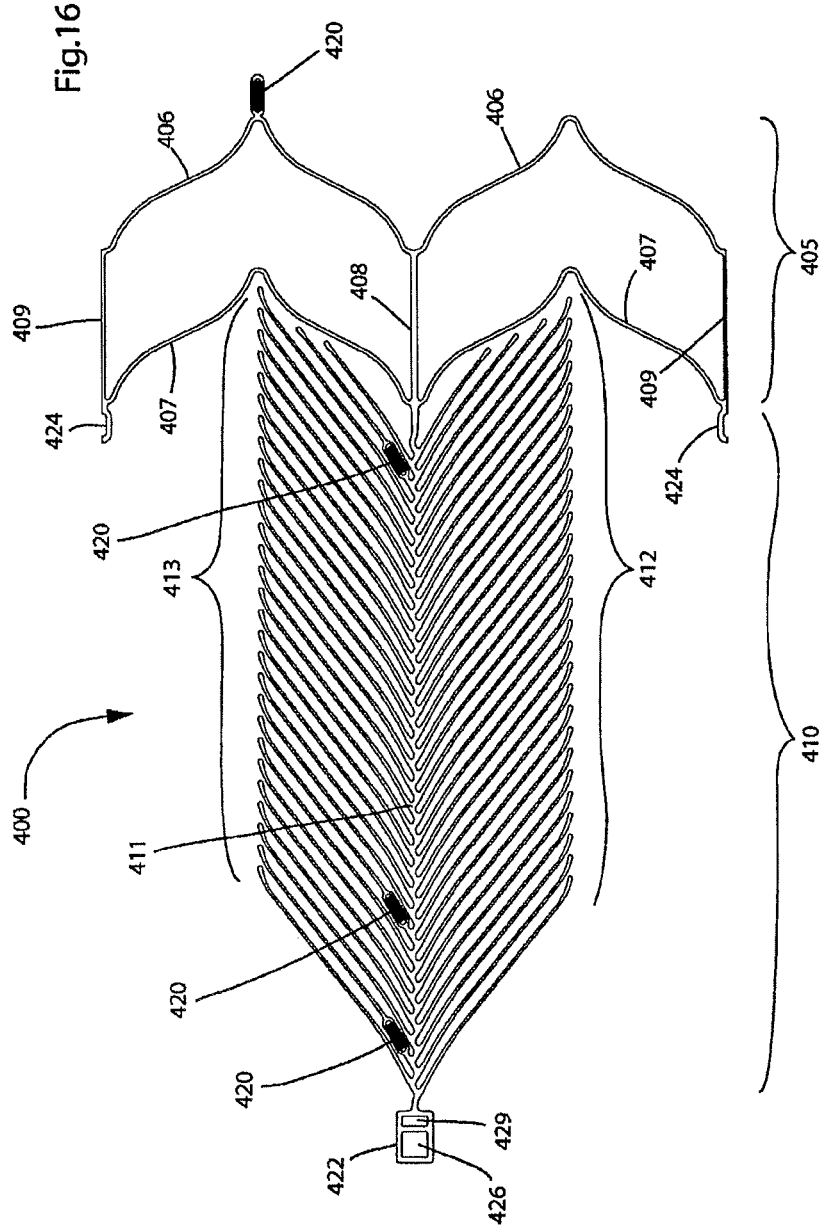

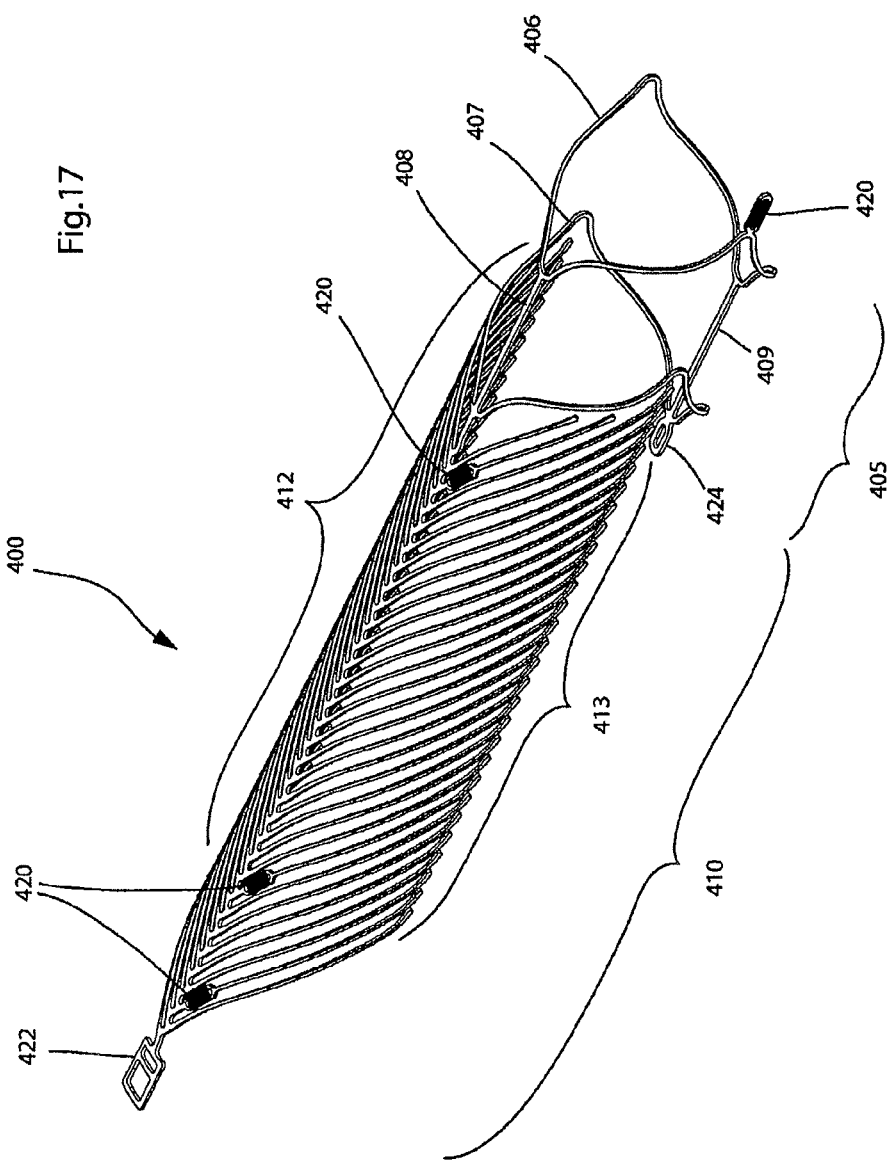

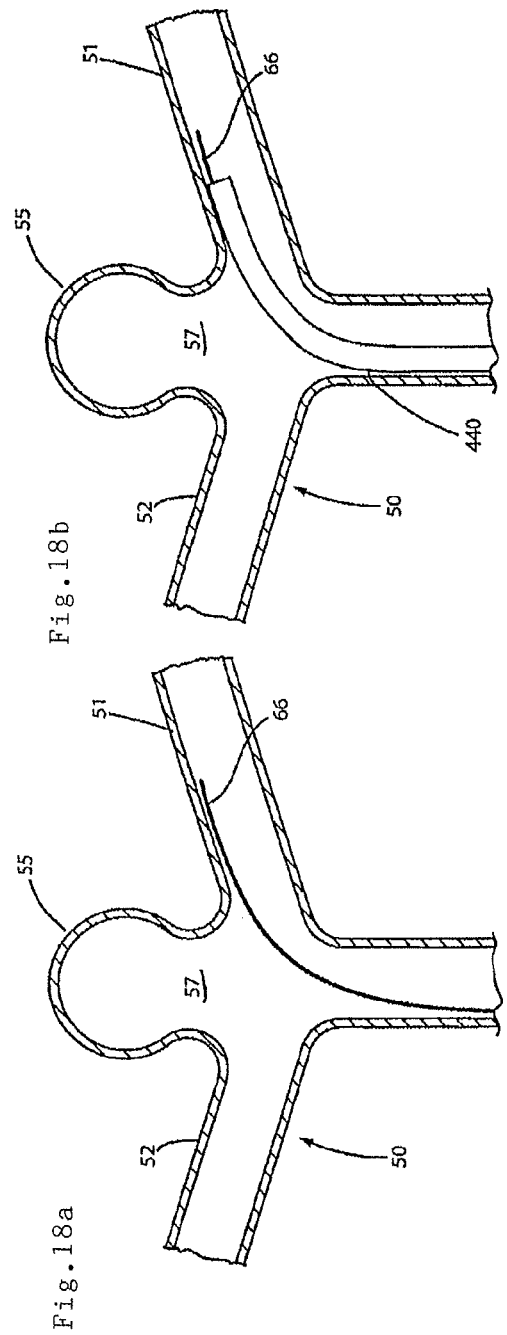

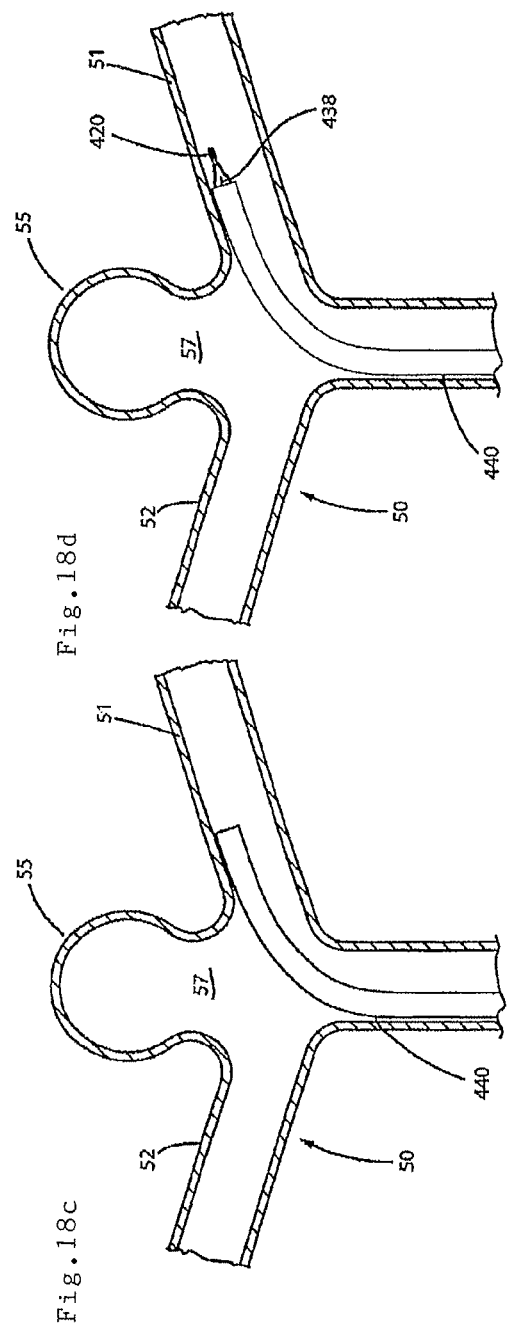

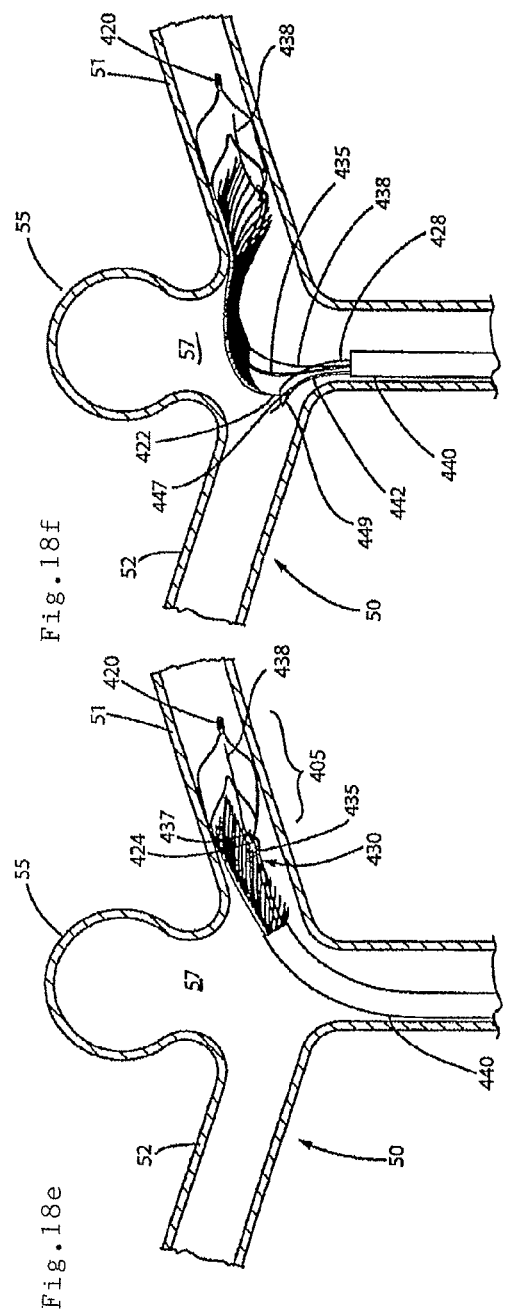

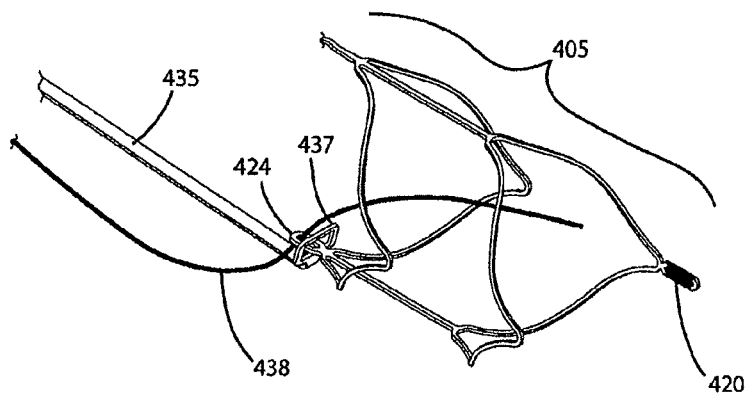
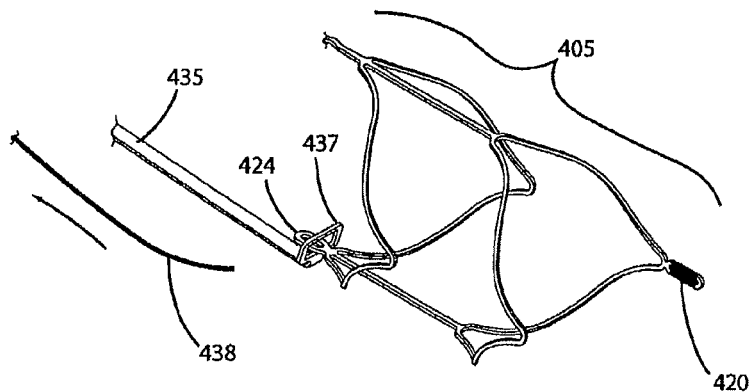
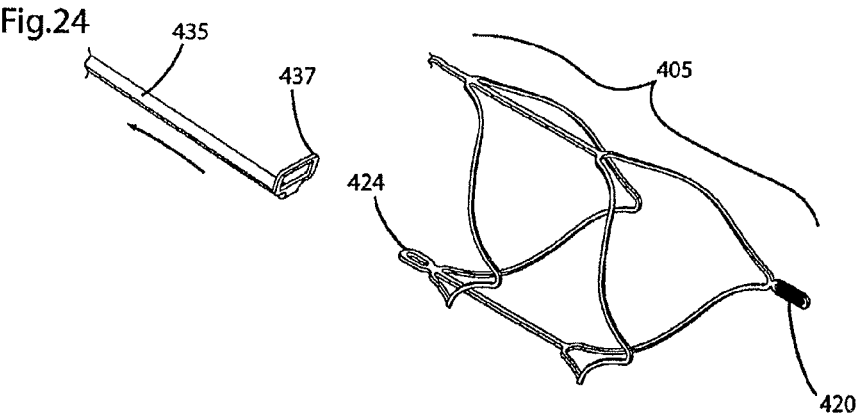

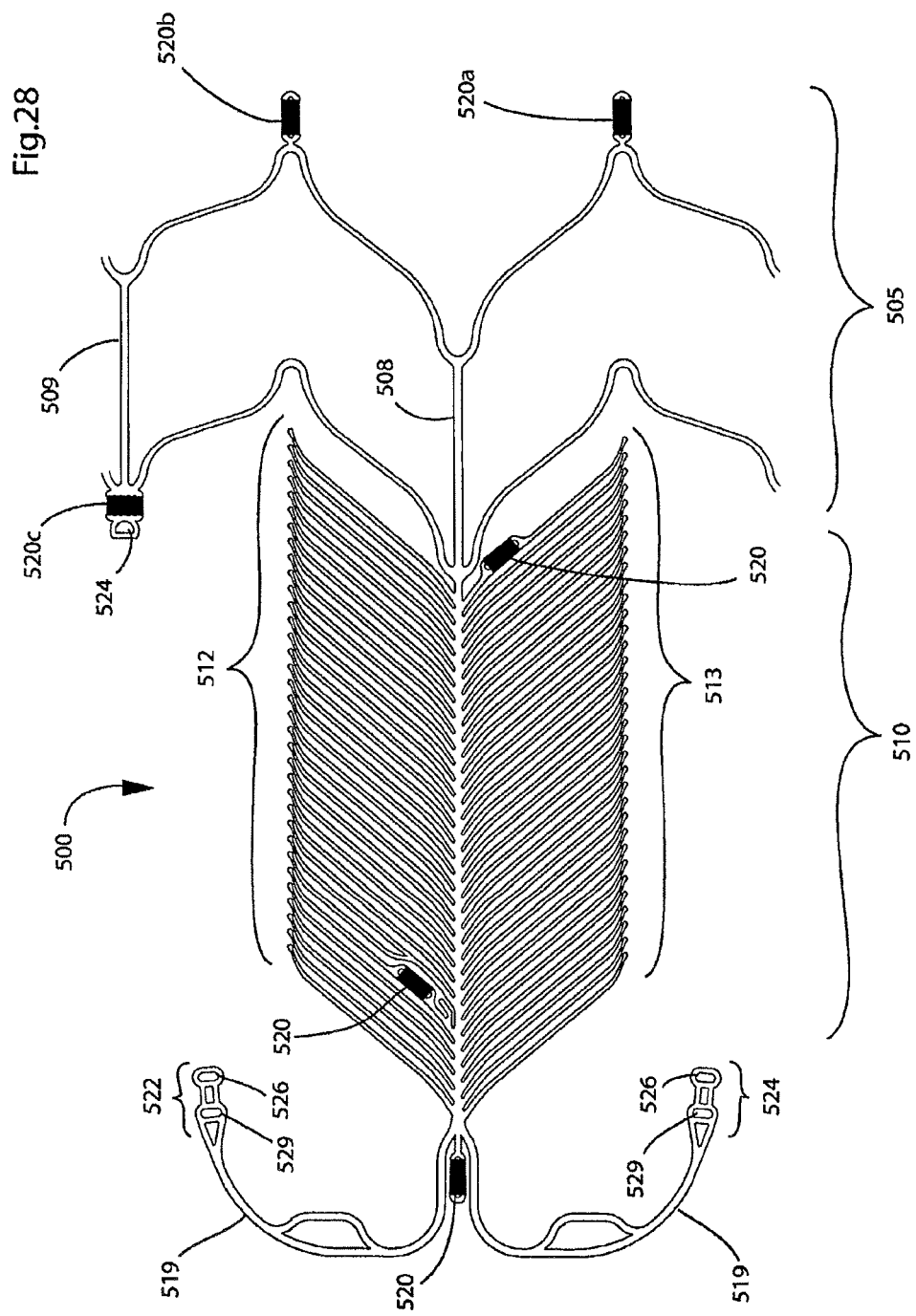

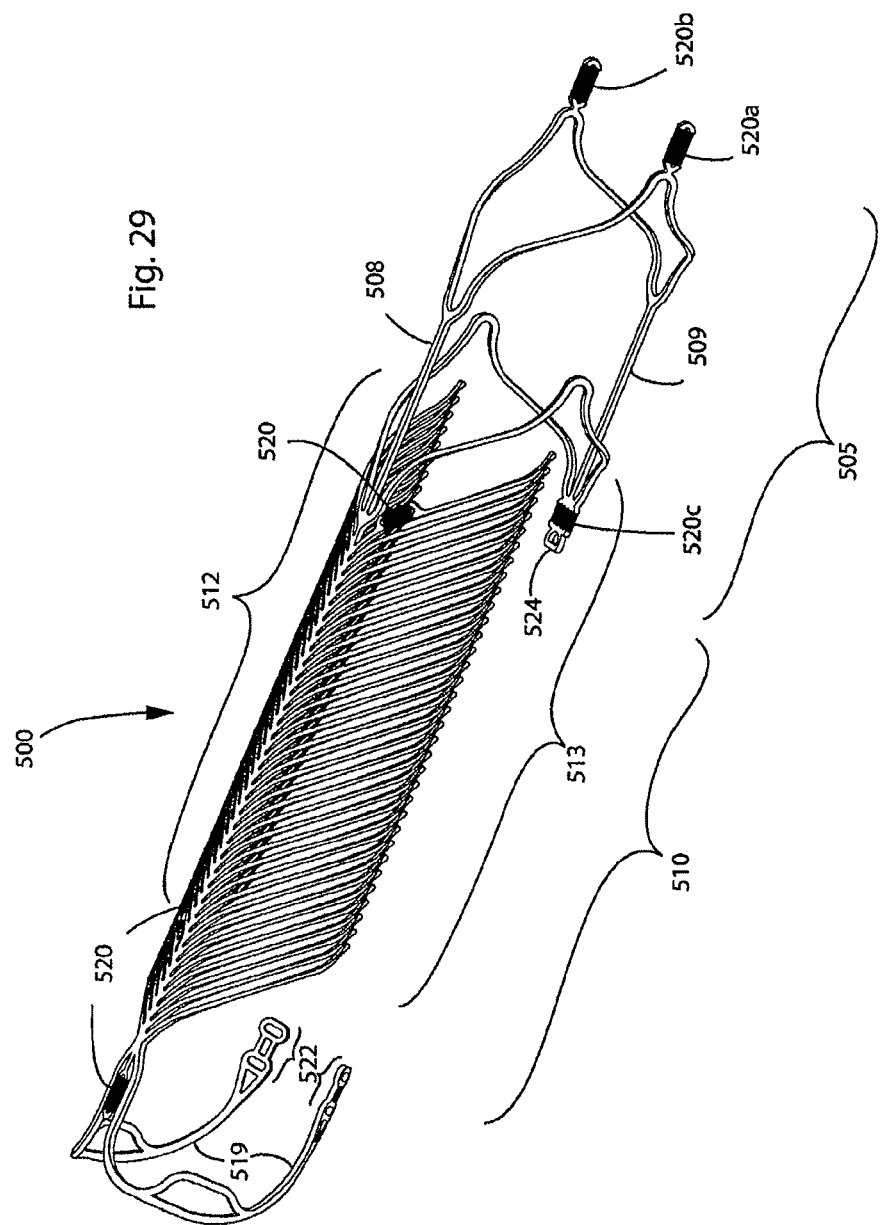

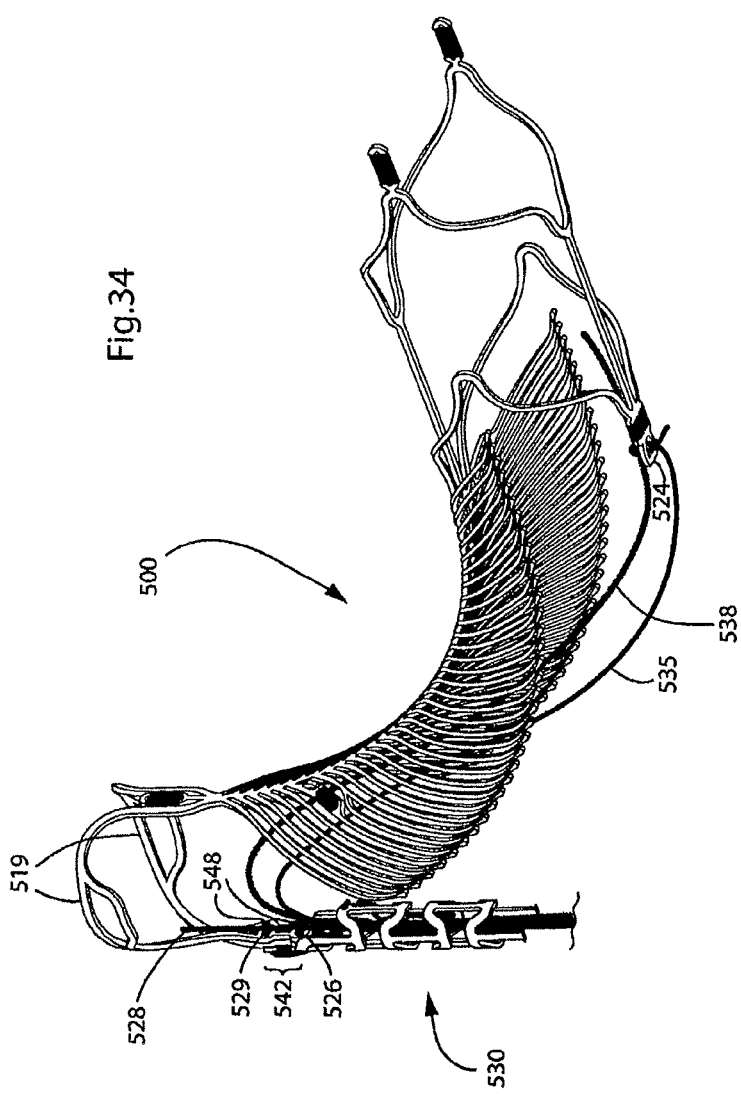
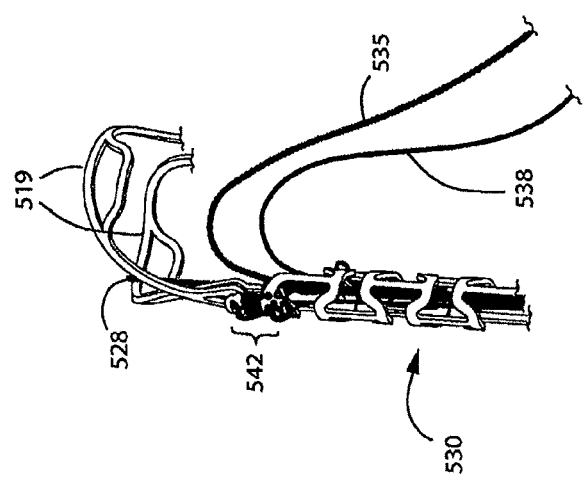
Fig.34
Fig.35

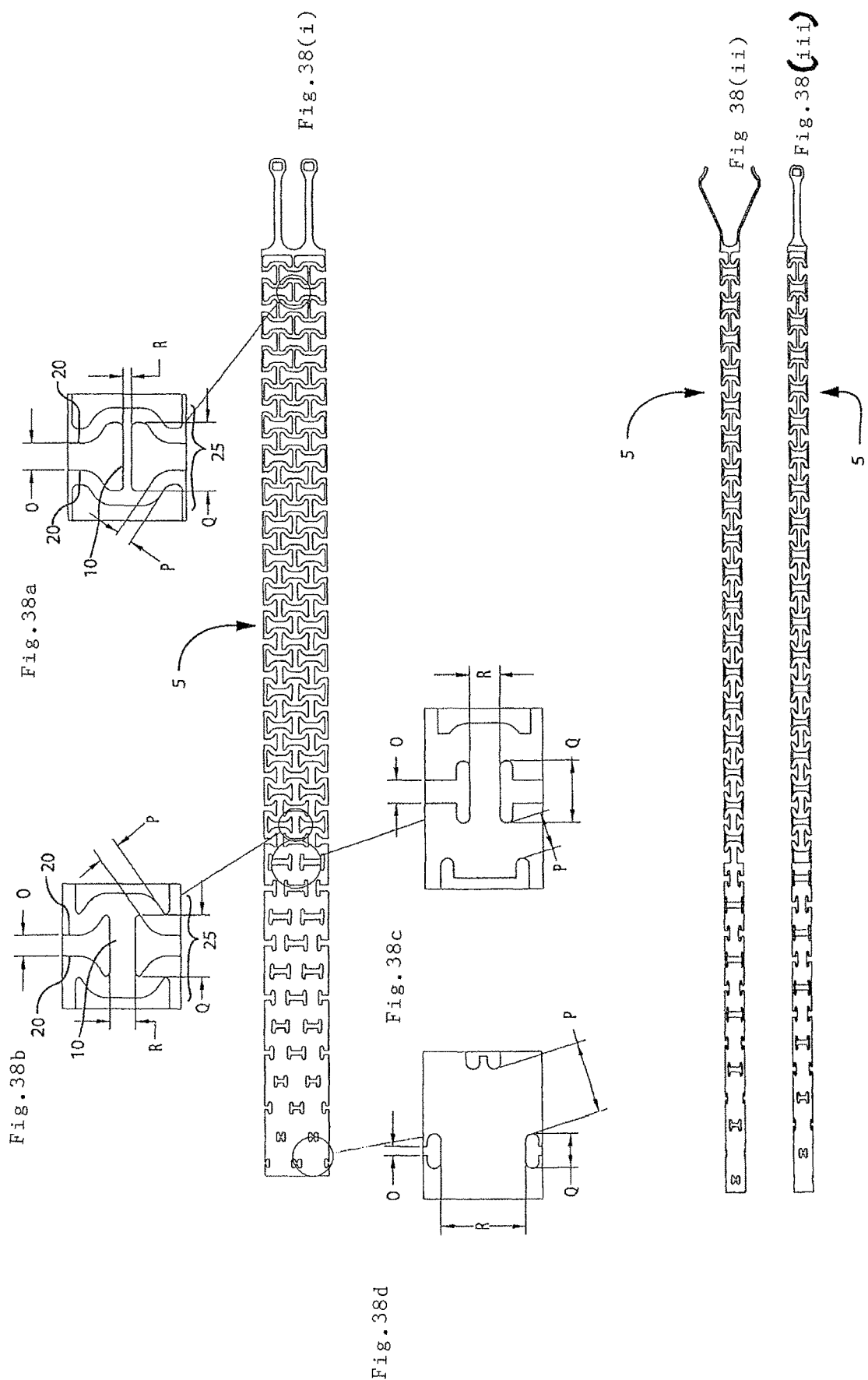

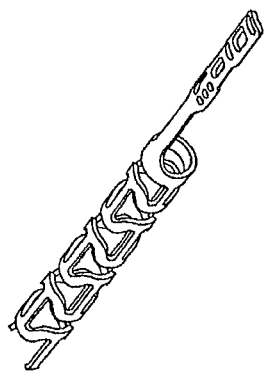
Fig.40d
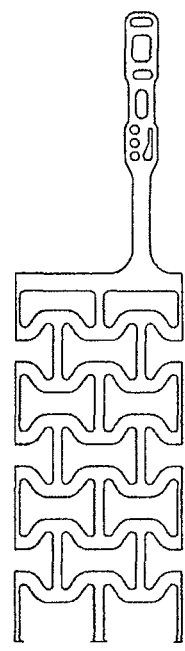
Fig.40a
Fig.40b
Fig.40c

ENDOVASCULAR PROSTHESIS AND DELIVERY DEVICE

CROSS-REFERENCE TO RELATED APPLICATION

The present application is a continuation of U.S. patent application Ser. No. 14/065,788, filed Oct. 29, 2013, now U.S. Pat. No. 9,056,024, issued Jun. 16, 2015, which is a continuation of International Application No. PCT/CA2012/000379, which was published in English and designated the U.S., which claims benefit of provisional U.S. Patent Appln. No. 61/457,604 and provisional U.S. Patent Appln. No. 61/457,605, each filed Apr. 29, 2011, the contents of all incorporated herein by reference.

BACKGROUND OF THE INVENTION

Field of the Invention

In one of its aspects, the present invention relates to an endovascular prosthesis. In another of its aspects, the present invention relates to a method of treating an aneurysm in a patient. In another of its aspects, the present invention relates to an endovascular prosthesis delivery device. Other aspects of the invention will be apparent to those of skill in the art having in hand the present specification.

Description of the Prior Art

As is known in the art, an aneurysm is an abnormal bulging outward in the wall of an artery. In some cases, the bulging may be in the form of a smooth bulge outward in all directions from the artery—this is known as a "fusiform aneurysm". In other cases, the bulging may be in the form of a sac arising from an arterial branching point or from one side of the artery—this is known as a "saccular aneurysm".

While aneurysms can occur in any artery of the body, it is usually those which occur in the brain which lead to the occurrence of a stroke. Most saccular aneurysms which occur in the brain have a neck which extends from the cerebral blood vessel and broadens into a pouch which projects away from the vessel.

The problems caused by such aneurysms can occur in several different ways. For example, if the aneurysm ruptures, blood enters the brain or the subarachnoid space (i.e., the space closely surrounding the brain)—the latter is known as an aneurysmal subarachnoid hemorrhage. This is followed by one or more of the following symptoms: nausea, vomiting, double vision, neck stiffness and loss of consciousness. Aneurysmal subarachnoid hemorrhage is an emergency medical condition requiring immediate treatment. Indeed, 10-15% of patients with the condition die before reaching the hospital for treatment. More than 50% of patients with the condition will die within the first thirty days after the hemorrhage. Of those patients who survive, approximately half will suffer a permanent stroke. Some of these strokes occur one to two weeks after the hemorrhage itself from vasospasm in cerebral vessels induced by the subarachnoid hemorrhage. Aneurysms also can cause problems which are not related to bleeding although this is less common. For example, an aneurysm can form a blood clot within itself which can break away from the aneurysm and be carried downstream where it has the potential to obstruct an arterial branch causing a stroke (e.g., an ischemic stroke). Further, the aneurysm can also press against nerves (this has the potential of resulting in paralysis or abnormal sensation of one eye or of the face) or the adjacent brain (this has the potential of resulting in seizures).

Given the potentially fatal consequences of the aneurysms, particularly brain aneurysms, the art has addressed treatment of aneurysms using various approaches.

Generally, aneurysms may be treated from outside the blood vessels using surgical techniques or from the inside using endovascular techniques (the latter falls under the broad heading of interventional (i.e., non-surgical) techniques).

Surgical techniques usually involve a craniotomy requiring creation of an opening in the skull of the patient through which the surgeon can insert instruments to operate directly on the brain. In one approach, the brain is retracted to expose the vessels from which the aneurysm arises and then the surgeon places a clip across the neck of the aneurysm thereby preventing arterial blood from entering the aneurysm. If there is a clot in the aneurysm, the clip also prevents the clot from entering the artery and obviates the occurrence of a stroke. Upon correct placement of the clip the aneurysm will be obliterated in a matter of minutes. Surgical techniques are the most common treatment for aneurysms. Unfortunately, surgical techniques for treating these conditions are regarded as major surgery involving high risk to the patient and necessitate that the patient have strength even to have a chance to survive the procedure.

As discussed above, endovascular techniques are non-surgical techniques and are typically performed in an angiography suite using a catheter delivery system. Specifically, known endovascular techniques involve using the catheter delivery system to pack the aneurysm with a material which prevents arterial blood from entering the aneurysm—this technique is broadly known as embolization. One example of such an approach is the Guglielmi Detachable Coil which involves intra-aneurysmal occlusion of the aneurysm via a system which utilizes a platinum coil attached to a stainless steel delivery wire and electrolytic detachment. Thus, once the platinum coil has been placed in the aneurysm, it is detached from the stainless steel delivery wire by electrolytic dissolution. Specifically, the patient's blood and the saline infusate act as the conductive solutions. The anode is the stainless steel delivery wire and the cathode is the ground needle which is placed in the patient's groin. Once current is transmitted through the stainless steel delivery wire, electrolytic dissolution will occur in the uninsulated section of the stainless steel detachment zone just proximal to the platinum coil (the platinum coil is of course unaffected by electrolysis). Other approaches involve the use of materials such as cellulose acetate polymer to fill the aneurysm sac. While these endovascular approaches are an advance in the art, they are disadvantageous. Specifically, the risks of these endovascular approaches include rupturing the aneurysm during the procedure or causing a stroke (e.g., an ischemic stroke) due to distal embolization of the device or clot from the aneurysm. Additionally, concern exists regarding the long term results of endovascular aneurysm obliteration using these techniques. Specifically, there is evidence of intra-aneurysmal rearrangement of the packing material and reappearance of the aneurysm on follow-up angiography.

One particular type of brain aneurysm which has proven to be very difficult to treat, particularly using the surgical clipping or endovascular embolization techniques discussed above occurs at the distal basilar artery. This type of aneurysm is a weak outpouching, usually located at the terminal bifurcation of the basilar artery. Successful treatment of this type of aneurysm is very difficult due, at least in part, to the imperative requirement that all the brainstem perforating vessels be spared during surgical clip placement.

Unfortunately, there are occasions when the size, shape and/or location of an aneurysm make both surgical clipping and endovascular embolization not possible for a particular patient. Generally, the prognosis for such patients is not good.

Accordingly, while the prior art has made advances in the area of treatment of aneurysms, there is still room for improvement, particularly in endovascular embolization since it is such an attractive alternative to major surgery.

In International Publication Number WO 99/40873 [Marotta et al. (Marotta)], published Aug. 19, 1999, there is taught a novel endovascular approach useful in blocking of an aneurysmal opening, particularly those in saccular aneurysms, leading to obliteration of the aneurysm. The approach is truly endovascular in that, with the endovascular prosthesis taught by Marotta, there is no requirement to pack the aneurysmal sac with a material (e.g., such is used with the Guglielmi Detachable Coil). Rather, the endovascular prosthesis taught by Marotta operates on the basis that it serves to block the opening to the aneurysmal sac thereby obviating the need for packing material. Thus, the endovascular prosthesis taught by Marotta is an important advance in the art since it obviates or mitigates many of the disadvantages of the prior art. The endovascular prosthesis taught by Marotta comprises a leaf portion capable of being urged against the opening of the aneurysm thereby closing the aneurysm. In the endovascular prosthesis taught by Marotta, the leaf portion is attached to, and independently moveable with respect to, a body comprising at least one expandable portion. The expandable portion is expandable from a first, unexpanded state to a second, expanded state with a radially outward force thereon. Thus, the body serves the general purpose of fixing the endovascular prosthesis in place at a target body passageway or vascular lumen in the vicinity at which the aneurysmal opening is located and the leaf portion serves the purpose of sealing the aneurysmal opening thereby leading to obliteration of the aneurysm. Thus, as taught by Marotta, the leaf portion functions and moves independently of the body of the endovascular prosthesis.

While the endovascular prosthesis taught by Marotta is a significant advance in the art, there is still room for improvement. Specifically, in the preferred embodiment of the endovascular prosthesis taught by Marotta, once the device is partially or fully deployed, for all intents and purposes, it is not possible to retrieve the prosthesis—e.g., for re-positioning. While this may not be a problem in most instances, there are occasions where the physician wishes to be able to retrieve the device so that it may be repositioned for optimum placement.

Accordingly, there remains a need in the art for an endovascular prosthesis that may be retrieved by the physician after it has been partially or fully deployed. It would be particularly advantageous to have a self-expanding endovascular prosthesis that may be retrieved by the physician after it has been partially or fully deployed.

SUMMARY OF THE INVENTION

It is an object of the present invention to obviate or mitigate at least one of the above-mentioned disadvantages of the prior art.

It is another object of the present invention to provide a novel endovascular prosthesis.

It is another object of the present invention to provide a novel endovascular prosthesis delivery device.

Accordingly, in one of its aspects, the present invention provides an endovascular prosthesis comprising a first expandable portion expandable from a first, unexpanded state to a second, expanded state to urge the first expandable portion against a vascular lumen; and a retractable leaf portion attached to the first expandable portion, the retractable leaf portion comprising at least one spine portion and a plurality of rib portions attached to the spine portion, longitudinally adjacent pairs of rib portions being free of interconnecting struts.

In another of its aspects, the present invention provides an endovascular prosthesis delivery device comprising a tubular member having a distal portion and a proximal portion, the distal portion having a porous surface defined by a plurality of circumferential rings, adjacent pairs of circumferential rings being interconnected by at least one longitudinal strut, the porous surface comprising a decreasing gradient of longitudinal strut circumferential width between longitudinal struts connected to opposed sides of a single circumferential ring in a direction from the proximal portion to the distal portion.

In another of its aspects, the present invention provides an endovascular prosthesis delivery device comprising a tubular member having a distal portion and a proximal portion, the distal portion having a porous surface defined by a plurality of circumferential rings, adjacent pairs of circumferential rings being interconnected by at least one longitudinal strut, the porous surface comprising a increasing porosity in a direction from the proximal portion to the distal portion.

In a preferred embodiment, the porous surface of the delivery device comprises a cover layer, preferably made of a polymer and/or preferably disposed substantially continuously over the porous surface, to reduce friction between the delivery device and the inner surface of a delivery catheter, facilitating a low force delivery of the endovascular prosthesis. The nature of the cover layer will be described in more detail hereinbelow.

Thus, the present inventors have discovered a novel endovascular prosthesis that can be unsheathed and re-sheathed for repositioning of the endovascular prosthesis prior to final deployment thereof. This provides the clinician with a significant advantage over the prior art devices described above. The present endovascular prosthesis comprises a first expandable portion expandable from a first, unexpanded state to a second, expanded state to urge the first expandable portion against the wall of the vascular lumen such as an artery. The endovascular prosthesis further comprises a retractable leaf portion attached to the first expandable portion; the retractable leaf portion serves to facilitate stasis and thrombotic occlusion of the aneurysm. The retractable leaf portion comprises at least one spine portion and a plurality of rib portions attached to the spine portion. Importantly, longitudinally adjacent pairs of rib portions are free of intricate connecting struts. The present inventors conducted a number of tests and have discovered that when connections are made between adjacent rib portions, the retractability of the leaf portion is significantly compromised and, in many cases, the leaf portion may not be retracted at all.

In addition, the present endovascular prosthesis is advantageous in that it has a natural tendency to flex in a manner such that the spine portion is on the outside of the bend. This is highly advantageous, especially when the device is implanted in a bifurcated body passageway. An additional advantage is that the orientation of the rib portions, coupled with the flex, particularly facilitates atraumatic and accurate delivery and deployment of the present endovascular prosthesis.

While not wishing to be bound by any particular theory or mode of action, it has been found that the rib portions of the present endovascular prosthesis are compressible whereas the spine in not compressible; therefore under an axial loading in the sheath, the rib portions have a tendency to compress and induce a bend that facilitates proper orientation during delivery in the correct direction.

In a highly advantageous embodiment, the present endovascular prosthesis is configured to be self-expanding. This means that the device may be sheathed or otherwise restrained prior to deployment and after initial delivery of the device, the sheath or restraint is partially retracted thereby allowing the device to self-expand. This allows for partial and progressive deployment of the device with the advantage that the clinician can re-sheath the device if initial deployment of the endovascular prosthesis is not in the correct position with respect to the target anatomy of the patient. In this context, it is also possible to achieve an additional rotational orientation of the present endovascular prosthesis by delivering the prosthesis using a 'torquable catheter'. This involves partially deploying the prosthesis to evaluate rotational orientation. If the rotation of the device relative to the aneurysm neck needs to be adjusted, the prosthesis may be retracted into the torquable catheter, torqued into the another orientation and then these steps are repeated until the prosthesis is deemed to be in the correct position relative to the aneurysm neck, after which the prosthesis may be fully unsheathed and detached from the delivery device using a number of techniques such as those described in more detail below. This is another highly advantageous feature of the present endovascular prosthesis.

Another aspect of the present invention relates to the provision of an endovascular prosthesis delivery device which comprises the tubular member having a distal portion and a proximal portion. The distal portion of the endovascular prosthesis has a porous surface made up of the number of circumferential rings with adjacent pairs of these rings being interconnected by one or more longitudinal struts. The porous surface in the distal portion of the endovascular prosthesis delivery device has a decrease in the width between a pair of the longitudinal struts connected to opposed sides of a given circumferential ring. This decrease in circumferential width of longitudinal strut runs in a direction from the proximal portion of the tubular member to the distal portion of the tubular member. Consequently, this means that the distal portion of the tubular member becomes progressively more flexible in a direction toward the distal most end of the tubular member. This feature facilitates navigating the endovascular prosthesis delivery device through tortuous anatomy while providing sufficient integrity and radial rigidity at the user end of the tubular member to be able to insert the device in the patient and navigate it completely to the target anatomy all the while obviating or mitigating kinking of the endovascular prosthesis delivery device. In a preferred embodiment, there is a decrease in the circumferential width between pairs of the circumferential rings running in a direction from proximal portion to the distal portion.

In a particularly preferred embodiment of the present endovascular prosthesis delivery device, the circumferential rings comprise a series of alternating peaks and valleys. In this preferred embodiment, it is further preferred that the longitudinal struts connect a valley from one circumferential ring with a valley in an adjacent circumferential ring. This so-called valley-valley connection embodiment is characterized by having the peaks in adjacent circumferential rings longitudinally aligned but unconnected. The advantage of this approach is that when the endovascular prosthesis delivery device is flexed to a certain degree, the adjacent peaks will contact each other prior to the endovascular prosthesis delivery device kinking, bending too much and yielding/breaking.

The present endovascular prosthesis is believed to be particularly useful in the treatment of aneurysms such as those described hereinabove and is therefore believed to provide a significant alternative to the conventional surgical techniques described hereinabove. Additionally, it is envisaged that the present endovascular prosthesis may be used in the treatment of certain aneurysms which are diagnosed as being inoperable. The present endovascular prosthesis also is believed to provide a significant advantage of current endovascular approaches such as the Guglielmi Detachable Coil described hereinabove. Specifically, since the present endovascular prosthesis does not rely on insertion into the aneurysm of a metal packing material (e.g., platinum coil), the risk of rupturing the aneurysm is mitigated as is the risk of intra-aneurysmal rearrangement of the metal packing material and subsequent reappearance of the aneurysm. Of course, those of skill in the art will recognize that there may be certain situations where the present endovascular prosthesis could be used in combination with Guglielmi Detachable Coils described hereinabove—e.g., to treat an aneurysm with a large neck in which an added structure across the neck (i.e., the present endovascular prosthesis) would help hold the coils with in the aneurysmal sac (this would obviate or mitigate the possibility of a coil exiting the aneurysm sac and causing an ischemic stroke).

BRIEF DESCRIPTION OF THE DRAWINGS

Embodiments of the present invention will be described with reference to the accompanying drawings, wherein like reference numerals denote like parts, and in which:

FIG. 1 a is an enlarged view of a portion of FIG. 1 identifying various elements in the design of the prosthesis;

FIG. 2 illustrates a perspective view of the endovascular prosthesis illustrated in FIG. 1;

FIG. 3 illustrates a top view of the endovascular prosthesis illustrated in FIGS. 1-2 coupled to a delivery device;

FIG. 4 illustrates delivery of the endovascular prosthesis illustrated in FIGS. 1-3 to occlude an aneurysm;

FIGS. 5-6 illustrate a portion of the endovascular prosthesis illustrated, in a transparent sheath, in FIGS. 1-4 as it is reversibly sheathed and unsheathed;

FIGS. 15(a)-15(d) illustrate further detail of coupling of the endovascular prosthesis illustrated in FIGS. 13-14 to the delivery device;

FIG. 16 illustrates a two-dimensional representation of a fourth embodiment of the present endovascular prosthesis;

FIG. 17 illustrates a perspective view of the endovascular prosthesis illustrated in FIG. 16;

FIGS. 18(a)-18(f), and 19-21 illustrate, in a step-wise manner, deployment of the endovascular prosthesis illustrated in FIGS. 16-17 in an aneurysm located at the junction of a bifurcated artery;

FIGS. 22-24 illustrate, in a step-wise manner, release of one end of the endovascular prosthesis illustrated in FIGS. 16-21 from the delivery device;

FIGS. 22-24) of the endovascular prosthesis illustrated in FIGS. 16-24;

FIG. 28 illustrates a two-dimensional representation of a fifth embodiment of the present endovascular prosthesis;

FIG. 29 illustrates a perspective view of the endovascular prosthesis illustrated in FIG. 28;

FIGS. 33-35 illustrate additional views of a delivery device used to deliver the endovascular prosthesis illustrated in FIGS. 28-32;

FIGS. 38(i)-(iii) illustrate a portion of a preferred embodiment of the present endovascular prosthesis delivery device (including enlarged views in FIGS. 38(a)-(d)); and FIGS. 39(a)-39(d), 40(a)-40(d), 41, 42(a)-42(c), and 43(a)-43(e) illustrate various views of various endovascular prosthesis delivery devices that are shown throughout FIGS. 1-37.

DETAILED DESCRIPTION OF THE PREFERRED EMBODIMENTS

Figure 1:
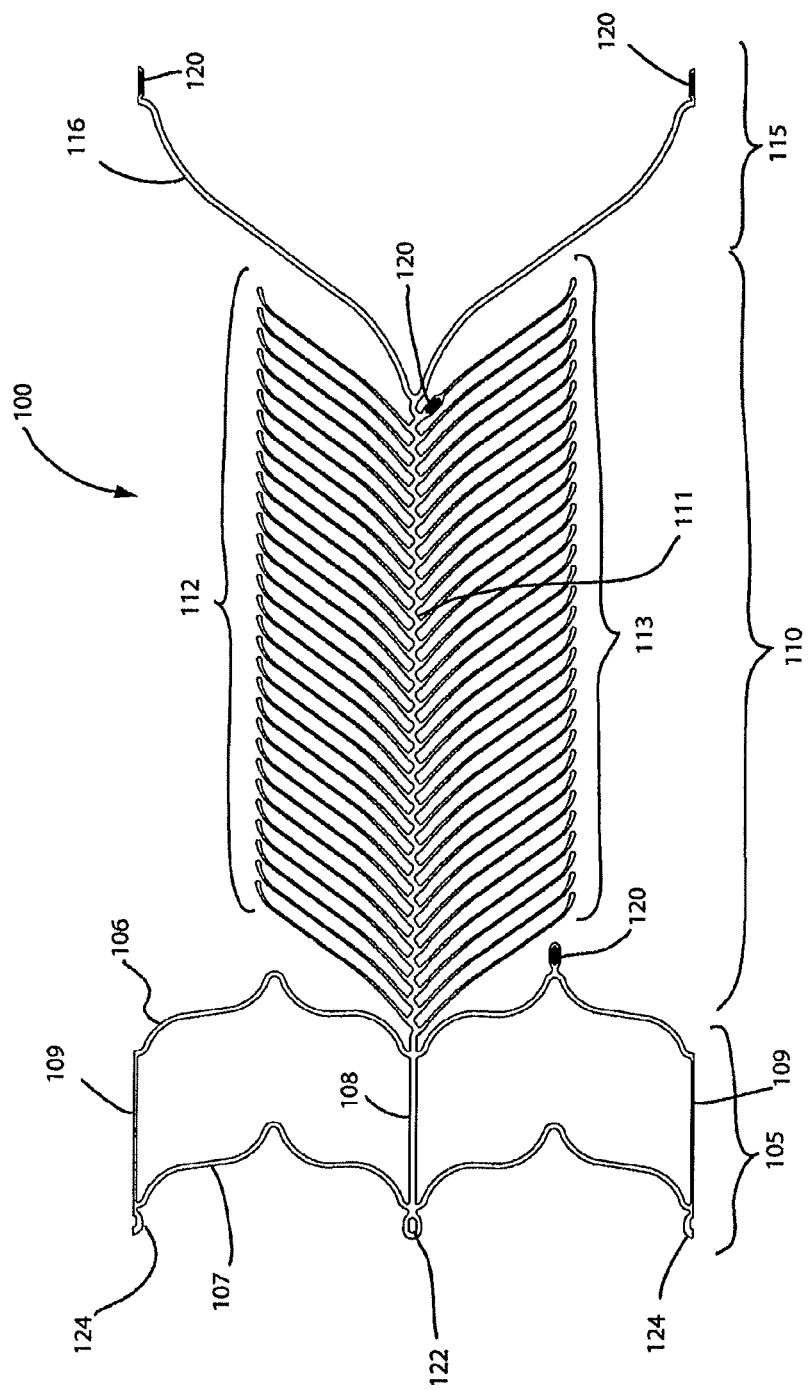
FIG. 1 illustrates a two-dimensional representation of a first embodiment of the present endovascular prosthesis.

In one of its aspects, the present invention relates to an endovascular prosthesis comprising: a first expandable portion expandable from a first, unexpanded state to a second, expanded state to urge the first expandable portion against a vascular lumen; and a retractable leaf portion attached to the first expandable portion, the retractable leaf portion comprising at least one spine portion and a plurality of rib portions attached to the spine portion, longitudinally adjacent pairs of rib portions being free of interconnecting struts. Preferred embodiments of this endovascular prosthesis may include any one or a combination of any two or more of any of the following features:

a single spine portion is connected to the first expandable portion;

the single spine portion comprises a row of rib portions connected to one side of the single spine portion;

the single spine portion comprises a pair of rows of rib portions, each row of rib portions connected to one side of the single spine portion;

the single spine portion comprises a pair of rows of rib portions connected to opposed sides of the single spine portion;

in two dimensions, each row of rib portions is a substantial mirror image of an adjacent row of rib portions along the single spine portion;

a first row of rib portions is connected at a plurality of first connection points to the single spine portion and a second row of rib portions is connected at a plurality of second connection points to the single spine portion, the plurality of first connection points and the plurality of second connection points being longitudinally aligned with respect to one another;

a first row of rib portions is connected at a plurality of first connection points to the single spine portion and a second row of rib portions is connected at a plurality of second connection points to the single spine portion, the plurality of first connection points and the plurality of second connection points being longitudinally staggered with respect to one another;

the single spine portion is linear;

the single spine portion is curvilinear;

the single spine portion is curved;

the single spine portion comprising an undulating pattern comprising alternating peaks and valleys;

at least some rib portions are connected to the peaks in the undulating pattern;

each rib portion is connected to a peak in the undulating pattern;

in two dimensions, each rib portion is configured substantially to form an acute angle with respect to a spine longitudinal axis of the single spine portion;

in two dimensions, each rib portion comprises a rib proximal portion, a rib distal portion and a rib intermediate portion disposed therebetween;

in two dimensions, each rib portion has a substantially constant circumferential width;

in two dimensions, each rib portion has a variable circumferential width;

in two dimensions, the rib intermediate portion has a circumferential width less than at least one of the rib proximal portion and the rib distal portion;

the rib intermediate portion has a circumferential width less than both of the rib proximal portion and the rib distal portion;

the rib proximal portion has a circumferential width in the range of from about 0.0010 to about 0.0120 inches;

the rib proximal portion has a circumferential width in the range of from about 0.0017 to about 0.0096 inches;

the rib proximal portion has a circumferential width in the range of from about 0.0024 to about 0.0072 inches;

the rib proximal portion is from about 1% to about 10% of the overall length of the rib portion;

the rib proximal portion is from about 2% to about 6% of the overall length of the rib portion;

the rib proximal portion is about 3% of the overall length of the rib portion;

rib intermediate portion has a circumferential width in the range of from about 0.0005 to about 0.0100 inches;

rib intermediate portion has a circumferential width in the range of from about 0.0011 to about 0.0062 inches;
rib intermediate portion has a circumferential width in the range of from about 0.0016 to about 0.0024 inches;
the rib intermediate portion is from about 25% to about 90% of the overall length of the rib portion;
the rib intermediate portion is from about 60% to about 90% of the overall length of the rib portion;
the rib intermediate portion is about 90% of the overall length of the rib portion;
rib distal portion has a circumferential width in the range of from about 0.0010 to about 0.0120 inches;
rib distal portion has a circumferential width in the range of from about 0.0013 to about 0.0072 inches;
rib distal portion has a circumferential width in the range of from about 0.0016 to about 0.0024 inches;
the rib distal portion is up to about 25% of the overall length of the rib portion;
the rib distal portion is from about 4% to about 16% of the overall length of the rib portion;
the rib distal portion is up to about 7% of the overall length of the rib portion;
the rib proximal portion is configured to form a rib proximal portion acute angle with respect to a longitudinal axis of the endovascular prosthesis;
the rib proximal portion acute angle is in the range of from about 15° to about 90°;
the rib proximal portion acute angle is in the range of from about 35° to about 60°;
the rib proximal portion acute angle is about 45°;
the rib distal portion is configured to form a rib distal portion angle with respect to a rib intermediate portion of the endovascular prosthesis;
the rib distal portion angle is in the range of from about 0° to about 120°;
the rib distal portion angle is in the range of from about 3° to about 60°;
the rib distal portion angle is about 8°;
the rib intermediate portion is configured to form a rib intermediate portion acute angle with respect to a longitudinal axis of the endovascular prosthesis;
the rib intermediate portion acute angle is in the range of from about 5° to about 140°;
the rib intermediate portion acute angle is in the range of from about 22° to about 86°;
the rib intermediate portion acute angle is about 45°;
the rib intermediate portion comprises: (i) a rib intermediate first portion connected to the rib proximal portion and configured to form a rib intermediate first portion acute angle with respect to a longitudinal axis of the endovascular prosthesis, and (ii) a rib intermediate second portion connected to the rib distal portion and configured to form a rib intermediate second portion acute angle with respect to a longitudinal axis of the endovascular prosthesis;
the rib intermediate first portion acute angle is less than the rib intermediate second portion acute angle;
the rib intermediate first portion acute angle is in the range of from about 5° to about 140°;
the rib intermediate first portion acute angle is in the range of from about 22° to about 66°;
the rib intermediate first portion acute angle is about 30°;
the rib intermediate second portion acute angle is in the range of from about 5° to about 140°;
the rib intermediate second portion acute angle is in the range of from about 42° to about 86°;
the rib intermediate second portion acute angle is about 60°;
the rib intermediate first portion has a circumferential width in the range of from about 0.0010 to about 0.0100 inches;
the rib intermediate first portion has a circumferential width in the range of from about 0.0014 to about 0.0062 inches;
the rib intermediate first portion has a circumferential width in the range of from about 0.0018 to about 0.0024 inches;
the rib intermediate first portion is from about 5% to about 25% of the overall length of the rib portion;
the rib intermediate first portion is from about 7% to about 17% of the overall length of the rib portion;
the rib intermediate first portion is about 9% of the overall length of the rib portion;
the rib intermediate second portion has a circumferential width in the range of from about 0.0005 to about 0.0070 inches;
the rib intermediate second portion has a circumferential width in the range of from about 0.0011 to about 0.0044 inches;
the rib intermediate second portion has a circumferential width in the range of from about 0.0016 to about 0.0018 inches;
the rib intermediate second portion is from about 25% to about 90% of the overall length of the rib portion;
the rib intermediate second portion is from about 53% to about 85% of the overall length of the rib portion;
the rib intermediate second portion is about 81% of the overall length of the rib portion;
in two dimensions, the rib distal portion of each rib portion is directed away from the first expandable portion;
in two dimensions, the rib distal portion of each rib portion is directed toward the first expandable portion;
in two dimensions, each rib portion is linear;
in two dimensions, each rib portion is curvilinear;
in two dimensions, each rib portion is curved;
in two dimensions, each rib portion comprises at least two sub-portions each sub-portion form a different angle with respect to a longitudinal axis of the endovascular prosthesis;
a pair of longitudinally adjacent rib portions are spaced at a connection point to the spine portion at a distance ranging from about 0.0254 mm to about 10 mm;
a pair of longitudinally adjacent rib portions are spaced at a connection point to the spine portion at a distance ranging from about 0.0254 mm to about 5 mm;
a pair of longitudinally adjacent rib portions are spaced at a connection point to the spine portion at a distance ranging from about 0.1400 mm to about 3 mm;
a pair of longitudinally adjacent rib portions are spaced at a connection point to the spine portion at a distance ranging from about 0.1400 mm to about 1 mm;
a pair of longitudinally adjacent rib portions are spaced at a connection point to the spine portion at a distance ranging from about 0.1400 mm to about 0.8 mm;
a pair of longitudinally adjacent rib portions are spaced at a connection point to the spine portion at a distance ranging from about 0.1400 mm to about 0.6 mm;
a pair of longitudinally adjacent rib portions are spaced at a connection point to the spine portion at a distance of about 0.254 mm;
in two dimensions, the at least one spine portion and the plurality of rib portions attached to the spine portion combine to occupy less than about 75% of a surface area of the retractable leaf portion;

in two dimensions, the at least one spine portion and the plurality of rib portions attached to the spine portion combine to occupy from about 5% to about 75% of a surface area of the retractable leaf portion;

in two dimensions, the at least one spine portion and the plurality of rib portions attached to the spine portion combine to occupy from about 5% to about 65% of a surface area of the retractable leaf portion;

in two dimensions, the at least one spine portion and the plurality of rib portions attached to the spine portion combine to occupy from about 10% to about 50% of a surface area of the retractable leaf portion;

in two dimensions, the at least one spine portion and the plurality of rib portions attached to the spine portion combine to occupy from about 15% to about 40% of a surface area of the retractable leaf portion;

in two dimensions, the at least one spine portion and the plurality of rib portions attached to the spine portion combine to occupy less than about 10% of a surface area of the retractable leaf portion;

in two dimensions, the at least one spine portion and the plurality of rib portions attached to the spine portion combine to occupy less than about 8% of a surface area of the retractable leaf portion;

in two dimensions, the at least one spine portion and the plurality of rib portions attached to the spine portion combine to occupy less than about 5% of a surface area of the retractable leaf portion;

in two dimensions, the at least one spine portion and the plurality of rib portions attached to the spine portion combine to occupy less than about 3% of a surface area of the retractable leaf portion;

the retractable leaf portion further comprises a cover layer connected to the plurality of rib portions;

the retractable leaf portion comprises less than 10 longitudinally spaced rib portions connected on one side of the spine portion;

the retractable leaf portion comprises less than 8 longitudinally spaced rib portions connected on one side of the spine portion;

the retractable leaf portion comprises less than 6 longitudinally spaced rib portions connected on one side of the spine portion;

the retractable leaf portion contains only 3 longitudinally spaced rib portions connected on one side of the spine portion;

the ratio of the perpendicular distance from the longitudinal axis to the distal tip portion of the rib portion to 50% of the circumference of the first expandable portion in the second, expanded state is in the range of from about 1:4 to about 1:1;

in two dimensions, the ratio of the perpendicular distance from the longitudinal axis to the distal tip portion of the rib portion to 50% of the circumference of the first expandable portion in the second, expanded state is in the range of from about 1:2.5 to about 1:1.5;

in two dimensions, the ratio of the perpendicular distance from the longitudinal axis to the distal tip portion of the rib portion to 50% of the circumference of the first expandable portion in the second, expanded state is about 5:9;

the at least one spine portion is curved about an axis transverse to a longitudinal axis of the endovascular prosthesis;

the at least one spine portion is curved about an axis substantially orthogonal to a longitudinal axis of the endovascular prosthesis;

the axis is opposed to the plurality of rib portions relative to the at least one spine portion;

the at least one spine portion comprises a first radius of curvature over the length of the at least one spine portion about an axis transverse to a longitudinal axis of the endovascular prosthesis;

the first radius of curvature is substantially constant from a proximal portion of the at least one spine portion to a distal portion of the at least one spine portion;

the first radius of curvature is variable from a proximal portion of the at least one spine portion to a distal portion of the at least one spine portion;

the first radius of curvature decreases from a proximal portion of the at least one spine portion to a distal portion of the at least one spine portion.

the retractable leaf portion comprises a second radius of curvature over the length of the at least one spine portion about a longitudinal axis of the endovascular prosthesis;

the second radius of curvature is substantially constant from a proximal portion of the retractable portion to a distal portion of the retractable portion;

the second radius of curvature is variable from a proximal portion of the retractable leaf portion to a distal portion of the retractable leaf portion;

the second radius of curvature increases from a proximal portion of the retractable leaf portion to a distal portion of the retractable leaf portion;

in an expanded configuration of the endovascular prosthesis, the retractable leaf portion comprises an arc of curvature about a longitudinal axis of the endovascular prosthesis in the range of from about 90° to about 360°;

in an expanded configuration of the endovascular prosthesis, the retractable leaf portion comprises an arc of curvature about a longitudinal axis of the endovascular prosthesis in the range of from about 120° to about 270°;

in an expanded configuration of the endovascular prosthesis, the retractable leaf portion comprises an arc of curvature about a longitudinal axis of the endovascular prosthesis in the range of from about 150° to about 250°;

in an expanded configuration of the endovascular prosthesis, the retractable leaf portion comprises an arc of curvature about a longitudinal axis of the endovascular prosthesis in the range of from about 175° to about 225°;

in an expanded configuration of the endovascular prosthesis, the retractable leaf portion comprises an arc of curvature about a longitudinal axis of the endovascular prosthesis of about 200°;

the first expandable portion has a diameter in the second, expanded state in range of from about 2 mm to about 40 mm;

the first expandable portion has a diameter in the second, expanded state in range of from about 2 mm to about 30 mm;

the first expandable portion has a diameter in the second, expanded state in range of from about 2 mm to about 20 mm;

the first expandable portion has a diameter in the second, expanded state in range of from about 2 mm to about 10 mm;

the first expandable portion has a diameter in the second, expanded state in range of from about 2.5 mm to about 5 mm;

a single spine portion is connected to the first expandable portion and a loop portion is connected to a distal portion of the single spine portion;

a single spine portion is connected to the first expandable portion and a split loop portion connected to a distal portion of the single spine portion;

the loop portion comprises a radioopaque portion;

the endovascular prosthesis further comprises a second expandable portion expandable from a first, unexpanded state to a second, expanded state to urge the first expandable portion against a vascular lumen;

the second expandable portion comprises a radioopaque portion;

the endovascular prosthesis is manufactured from a tubular starting material;

the endovascular prosthesis is manufactured from a tubular starting material on which a cutting technique has been applied;

the endovascular prosthesis is manufactured from a tubular starting material on which a laser cutting technique has been applied;

tubular wall has a radial thickness in the range of from about 0.0005 to about 0.0200 inches;

the tubular wall has a radial thickness in the range of from about 0.0015 to about 0.0100 inches;

the tubular wall has a radial thickness of about 0.0025 inches;

the first expandable portion comprises a radioopaque portion;

the prosthesis is constructed from a self-expanding material;

the prosthesis is constructed from a shape memory alloy;

the prosthesis is constructed from nitinol;

the prosthesis is constructed from a metallic material; and/or the prosthesis is constructed from a polymer material.

In one of its aspects, the present invention relates to an endovascular prosthesis delivery device comprising a tubular member having a distal portion and a proximal portion, the distal portion having a porous surface defined by a plurality of circumferential rings, adjacent pairs of circumferential rings being interconnected by at least one longitudinal strut, the porous surface comprising a decreasing gradient of longitudinal strut circumferential width between longitudinal struts connected to opposed sides of a single circumferential ring in a direction from the proximal portion to the distal portion. Preferred embodiments of this endovascular prosthesis delivery device may include any one or a combination of any two or more of any of the following features:

each circumferential ring comprises alternating peaks and valleys;

the at least one longitudinal strut connects a first valley in a first circumferential ring to a second valley in a second circumferential ring adjacent to the first circumferential ring;

the at least one longitudinal strut connects to a mid-point of the first valley;

the at least one longitudinal strut connects to a mid-point of the second valley;

the at least one longitudinal strut connects to: (i) a mid-point of the first valley, and (ii) a mid-point of the second valley;

the first circumferential ring and the second circumferential ring each comprise at least one pair of alternating peaks and valleys;

the first circumferential ring and the second circumferential ring each comprise at least two pairs of alternating peaks and valleys;

the endovascular prosthesis delivery device comprises a longitudinal strut for each peak;

the endovascular prosthesis delivery device comprises a longitudinal strut for each valley;

the endovascular prosthesis delivery device comprises a longitudinal strut for each pair of alternating peaks and valleys in first circumferential ring or the second circumferential ring;

the first circumferential ring and the second circumferential ring each comprise one pair of alternating peaks and valleys;

two longitudinal struts interconnect the first circumferential ring and the second circumferential ring;

the plurality of circumferential rings comprises a first circumferential ring, a second circumferential ring axially spaced from the first circumferential ring and a third circumferential ring axially spaced from the second circumferential ring;

the first circumferential ring and the third circumferential ring are spaced at a distance that is in the range from about 100% to about 300% of the diameter of the tubular member;

the first circumferential ring and the third circumferential ring are spaced at a distance that is in the range from about 175% to about 225% of the diameter of the tubular member;

the first circumferential ring and the third circumferential ring are spaced at a distance that is about 200% of the diameter of the tubular member;

the porous surface has a proximal porous portion and a distal porous portion disposed distally of the proximal porous portion;

the endovascular prosthesis delivery device comprises a first longitudinal strut disposed in the distal porous portion and a second longitudinal strut disposed in the proximal porous portion, with the proviso that a first longitudinal strut circumferential width of the first longitudinal strut is less than a second longitudinal strut circumferential width of the second longitudinal strut;

the first longitudinal strut circumferential width and the second longitudinal strut circumferential width each are in the range of from about 0.0010 in to about 0.0500 in;

the first longitudinal strut circumferential width and the second longitudinal strut circumferential width each are in the range of from about 0.0035 in to about 0.0300 in;

the first longitudinal strut circumferential width and the second longitudinal strut circumferential width each are in the range of from about 0.0045 in to about 0.0150 in;

the first longitudinal strut circumferential width is greater than about 0.0010 in and the second longitudinal strut circumferential width is less than about 0.0500 in;

the first longitudinal strut circumferential width is greater than about 0.0035 in and the second longitudinal strut circumferential width is less than about 0.0300 in;

the first longitudinal strut circumferential width is greater than about 0.0045 in and the second longitudinal strut circumferential width is less than about 0.0150 in;

the endovascular prosthesis delivery device comprises a first circumferential ring disposed in the distal porous portion and a second circumferential ring disposed in the proximal porous surface, with the proviso that a first axial width of the first circumferential ring is less than a second axial width of the second circumferential ring;

the first axial width and the second axial width each are in the range of from about 0.0010 in to about 0.0450 in;

the first axial width and the second axial width each are in the range of from about 0.0040 in to about 0.0325 in;

the first axial width and the second axial width each are in the range of from about 0.0050 in to about 0.0250 in;

the first axial width is greater than about 0.0010 in and the second axial width is less than about 0.0450 in;

the first axial width is greater than about 0.0040 in and the second axial width is less than about 0.0325 in;

the first axial width is greater than about 0.0050 in and the second axial width is less than about 0.0250 in;

the endovascular prosthesis delivery device comprises a first pair of adjacent circumferential rings disposed in the distal porous portion and a second pair of circumferential rings disposed in the proximal porous surface, with the proviso that a first minimum distance between the first pair of adjacent circumferential rings is greater than a second minimum distance between the second pair of adjacent circumferential rings;

both of the first minimum distance and the second minimum distance are in the range of from about 0.0010 in to about 0.0250 in;

both of the first minimum distance and the second minimum distance are in the range of from about 0.0025 in to about 0.0190 in;

both of the first minimum distance and the second minimum distance are in the range of from about 0.0040 in to about 0.0150 in;

the first minimum distance is less than about 0.0250 in and the second minimum distance is greater than about 0.0010 in;

the first minimum distance is less than about 0.0190 in and the second minimum distance is greater than about 0.0025 in;

the first minimum distance is less than about 0.0150 in and the second minimum distance is greater than about 0.0040 in;

the endovascular prosthesis delivery device comprises a first pair of adjacent circumferential rings disposed in the distal porous portion and a second pair of circumferential rings disposed in the proximal porous surface, with the proviso that a first maximum distance between the first pair of adjacent circumferential rings is greater than a second maximum distance between the second pair of adjacent circumferential rings;

both of the first maximum distance and the second maximum distance are in the range of from about 0.0050 in to about 0.0400 in;

both of the first maximum distance and the second maximum distance are in the range of from about 0.0075 in to about 0.0365 in;

both of the first maximum distance and the second maximum distance are in the range of from about 0.0090 in to about 0.0330 in;

the first minimum distance is less than about 0.0400 in and the second minimum distance is greater than about 0.0050 in;

the first minimum distance is less than about 0.0365 in and the second minimum distance is greater than about 0.0075 in;

the first minimum distance is less than about 0.0330 in and the second minimum distance is greater than about 0.0090 in;

the endovascular prosthesis delivery device further comprises an endovascular prosthesis connection portion attached to the distal portion;

the endovascular prosthesis connection portion comprises at least one elongate section comprising an intermediate section and a distal section for connection to the endovascular prosthesis;

at least one of the intermediate section and the distal section are angled with respect to a longitudinal axis of the endovascular prosthesis delivery device;

both of the intermediate section and the distal section are angled with respect to a longitudinal axis of the endovascular prosthesis delivery device;

the intermediate section and the distal section are angled with respect to one another;

the endovascular prosthesis connection portion comprises a pair of elongate sections comprising a first elongate section and a second elongate section;

the first elongate section comprises an endovascular prosthesis first attachment portion disposed at a distal end thereof;

the endovascular prosthesis first attachment portion comprises a first half of a first male-female connection system for receiving a second half of the first male-female connection system disposed on an endovascular prosthesis;

the first half of the first male-female connection system comprises a first male portion;

the second half of the first male-female connection system comprises a first female portion;

the first half of the first male-female connection system comprises a first female portion;

the second half of the first male-female connection system comprises a first male portion;

the first half of the first male-female connection is configured to receive a first endovascular prosthesis detachment member;

the second half of the first male-female connection is configured to receive a first endovascular prosthesis detachment member;

the first half and the second half of the first male-female connection are configured to receive a first endovascular prosthesis detachment member;

the first endovascular prosthesis detachment member comprises a first wire member;

the second elongate section comprises an endovascular prosthesis second attachment portion disposed at a distal end thereof;

the endovascular prosthesis second attachment portion comprises a first half of a second male-female connection system for receiving a second half of the second male-female connection system disposed on an endovascular prosthesis;

the first half of the second male-female connection system comprises a second male portion;

the second half of the second male-female connection system comprises a second female portion;

the first half of the second male-female connection system comprises a second female portion;

the second half of the second male-female connection system comprises a second male portion;

the first half of the second male-female connection is configured to receive a second endovascular prosthesis detachment member;

the second half of the second male-female connection is configured to receive a second endovascular prosthesis detachment member;

the first half and the second half of the second male-female connection are configured to receive a second endovascular prosthesis detachment member;

the endovascular prosthesis detachment member comprises a wire member;

the first elongate portion has a greater longitudinal length than the second elongate portion;

the second elongate portion has a greater longitudinal length than the first elongate portion; and/or the first elongate portion and the second elongate portion have a substantially equal longitudinal length.

With reference to FIGS. 1-2, there is illustrated an endovascular prosthesis 100. Endovascular prosthesis 100 comprises an expandable portion 105, a leaf portion 110 and a loop portion 115. Expandable portion 105 comprises a pair of undulating circumferential rings 106,107 that are interconnected to one another by a pair of longitudinal struts 108,109.

Leaf portion 110 comprises a spine portion 111 to which is connected a first row of rib portions 112 on one side thereof and a second row of rib portions 113 on an opposed side thereof. As can be seen, spine portion 111 comprises an undulating configuration (see also FIG. 1a for an enlarged view of this feature). Individual ribs in each of rows 112,113 are connected to the peaks of the undulating pattern formed by spine portion 111. This results in the connection points of individual rib portions in rows 112,113 being longitudinally offset with respect to one another.

The specifications for each rib portion in rows 112 and 113 are preferred to be those mentioned above. Loop portion 115 comprises a single loop portion 116, the function of which will be described in more detail below.

Endovascular prosthesis 100 further comprises a series of radiopaque markers 120 disposed at various positions on prosthesis 100.

Expansible portion 105 comprises a pair of loop portions 122,124 for connection to a delivery system (discussed below).

With reference to FIG. 1a, there is illustrated an enlarged view of a portion of endovascular device 100. The following is a concordance of terms used in FIG. 1a (while the terms are illustrated with reference to endovascular device 100, the also apply to endovascular devices 200, 300, 400, 500 and 600 described in more detail hereinbelow) and elsewhere in this specification:

| | | |
|---|---|---|
| A | root angle | rib proximal portion acute angle |
| B | lead in angle | rib intermediate first portion acute angle |
| C | rib angle | rib intermediate second portion acute angle |
| D | tip angle | rib distal portion acute angle |
| W | root width | rib proximal portion |
| X | lead in width | rib intermediate first portion |
| Y | rib width | rib intermediate second portion |
| Z | tip width | rib distal portion |

With reference to FIG. 3, endovascular prosthesis 100 is connected to a delivery device 130. The details of delivery device 130 will be discussed in further detail below. For present purposes, delivery device 130 comprises at its distal end a pair of arms 135 (only one arm is shown in FIG. 3). Each arm 135 of delivery device 130 is connected to loop portion 122 or 124 of expansible portion 105 as shown in FIG. 3. A delivery catheter 140 covers delivery device 130.

With reference to FIG. 4, further details are provided on connection of delivery device 130 to endovascular prosthesis 100 and deployment of the latter.

Thus, delivery device 130 comprises a porous tube 132 at the distal portion of which may be found arms 135. One arm 135 is connected to loop 122 of expansible portion 105 in a male-female arrangement while the other arm 135 is connected to loop portion 124 also in a male-female relationship. The connection between arms 135 and loop portions 122,124 is maintained as shown in FIG. 4 by a pair of wires 137.

As shown in FIG. 4, endovascular prosthesis 100 is delivered to a body passageway 10 (i.e., an artery) having an aneurysm 15 with an aneurysmal opening 17. In the illustrated embodiment, endovascular prosthesis 100 is a so-called self-expanding device. This means that when sheath 140 is retracted, endovascular prosthesis 100 will expand to its deployed state.

In the illustrated embodiment, endovascular prosthesis 100 is positioned incorrectly with respect to aneurysm 15, particularly the aneurysmal opening 17. Specifically, the clinical goal is to have leaf portion 115 covering aneurysmal opening 17 of aneurysm 15, ultimately leading to occlusion of aneurysm 15. As shown in FIG. 4, the clinical goal has not been achieved.

One of the specific advantages of the present invention generally and the endovascular prosthesis specifically is that the prosthesis may be refracted into the sheath after it has been completely unsheathed and before it has been fully released and deployed. A device that is retracted and partially unsheathed is shown schematically in FIGS. 5 and 6, respectively.

Thus, in FIG. 5 sheath 140 is extended to cover leaf portion 115 of endovascular prosthesis 100. While, in the illustrated embodiment, loop portion 116 emanates from sheath 140 in FIG. 5, the entire device could be retracted into sheath 140, if desired. The orientation and design of the rib portions in leaf portion 115 facilitate retraction of leaf portion 105 into sheath 140, for example, by allowing crisscrossing of the distal portions of respective rib portions in rows 112,113—this is a particularly advantageous feature of the present endovascular prosthesis generally.

As shown in FIG. 5, re-sheathing of endovascular prosthesis 100 is achieved by relative movement between endovascular prosthesis 100 and sheath 140 in the direction of arrow A. When it is desired to unsheath endovascular prosthesis 100 (for the first time or otherwise), sheath 140 is moved relative to endovascular prosthesis in the direction of arrow B as shown in FIG. 6.

The ability to sheath, unsheath, re-sheath, etc. endovascular prosthesis 100 as shown in FIGS. 5 and 6 is a distinct advantage of the present endovascular prosthesis generally since it allows the clinician to optimize the position of leaf portion 115 relative to aneurysmal opening 17 of aneurysm 15, even after endovascular prosthesis 100 has been partially or fully unsheathed. Furthermore, the sheathing, unsheathing, re-sheathing, etc. . . . feature also allows the clinician to evaluate the size (diameter and length) of the endovascular prosthesis relative to the patient anatomy and if the sizing is not satisfactory the clinician can fully remove the endovascular prosthesis and exchange it for a correctly sized device while maintaining the sheath in the patient at the target site.

Figure 7:
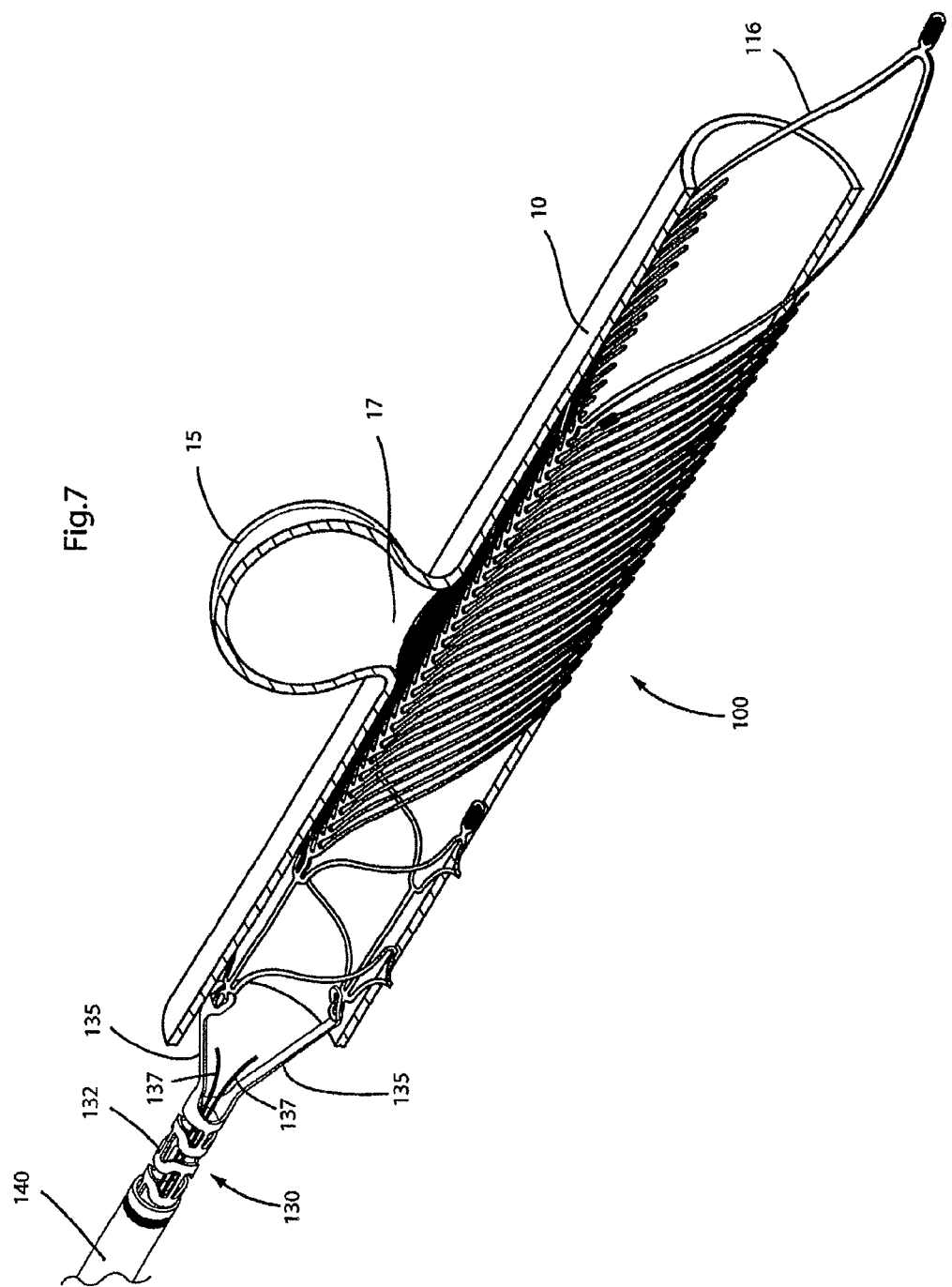
FIG. 7 illustrates the endovascular prosthesis illustrated in FIGS. 1-6 after it has been released from the delivery device and is in the correct position to treat the aneurysm.

The optimum position of endovascular prosthesis 100 is shown in FIG. 7 wherein leaf portion 115 occludes aneurysmal opening 17 of aneurysm 15. The term "occlude" is used in a broad sense and generally means leaf portion 115 covers aneurysmal opening 17 of aneurysm 15. While not wishing to be bound by any theory or particular mode of action, it is believed that this action of leaf portion 115 creates a pressure drop between aneurysm 15 and the parent vessel which leads ultimately to occlusion and healing. Single loop 116 of loop portion 115 serves to improve apposition of leaf portion 110 in body passageway 10.

Figure 8:
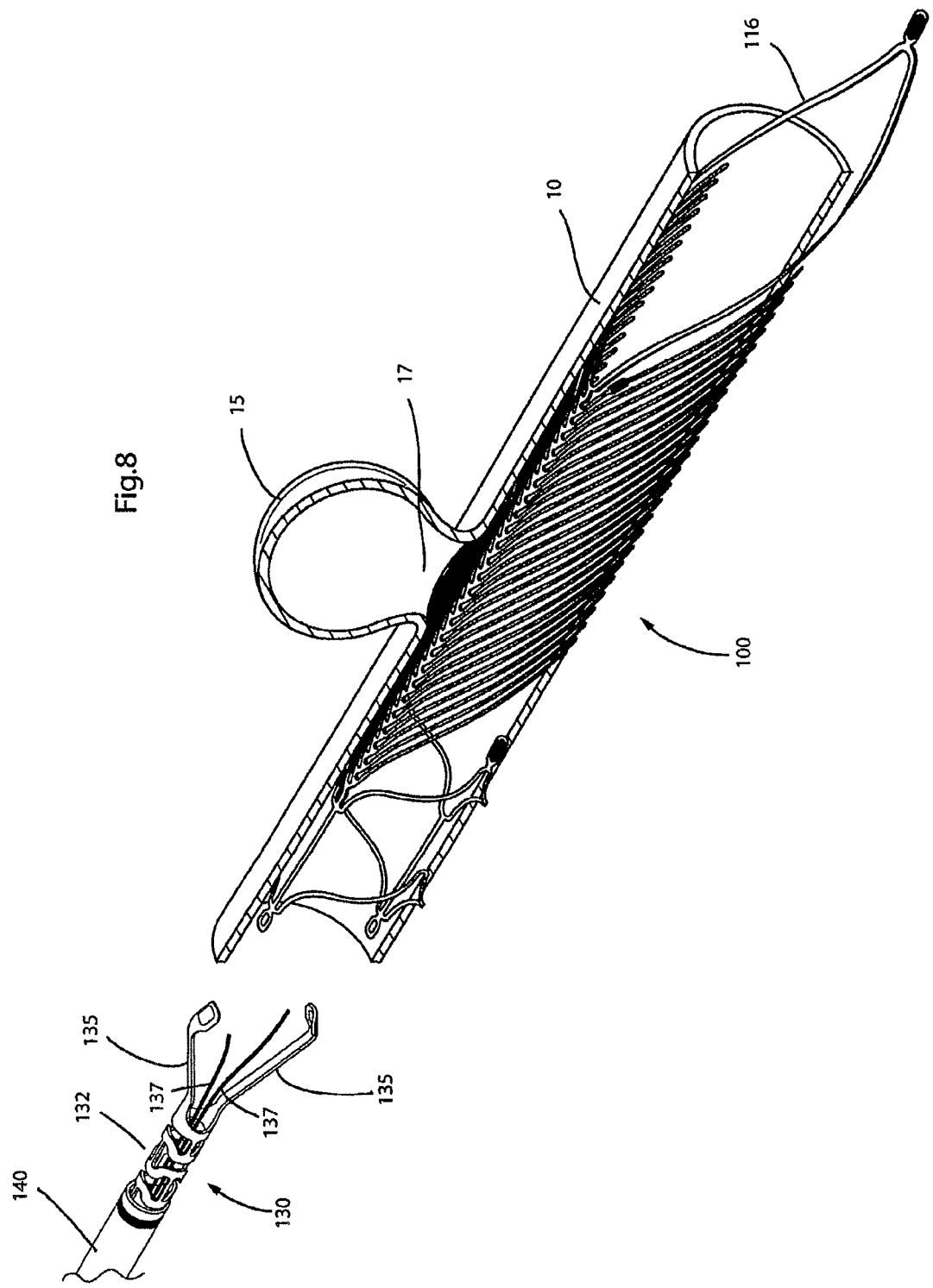
FIG. 8 illustrates the endovascular prosthesis illustrated in FIGS. 1-7 after it has been deployed and is occluding an aneurysm (also, the delivery device is pulled away from the endovascular prosthesis)

Once endovascular prosthesis 100 is in the correct position (this may be confirmed by the clinical use of conventional radiography and observing the position of radioopaque markers 120 relative to the target anatomy), endovascular prosthesis 100 is released from delivery device 130. This is achieved by retracting wires 137 (initial retraction is shown in FIG. 7) which allows arms 135 of delivery device 130 to be released from loops 122,124 of expansible portion 105 of endovascular prosthesis 100. Delivery device 130 and sheath 140 may then be withdrawn from the patient. Leaving the correctly deployed endovascular prosthesis 100 implanted as shown in FIG. 8.

Figure 9:
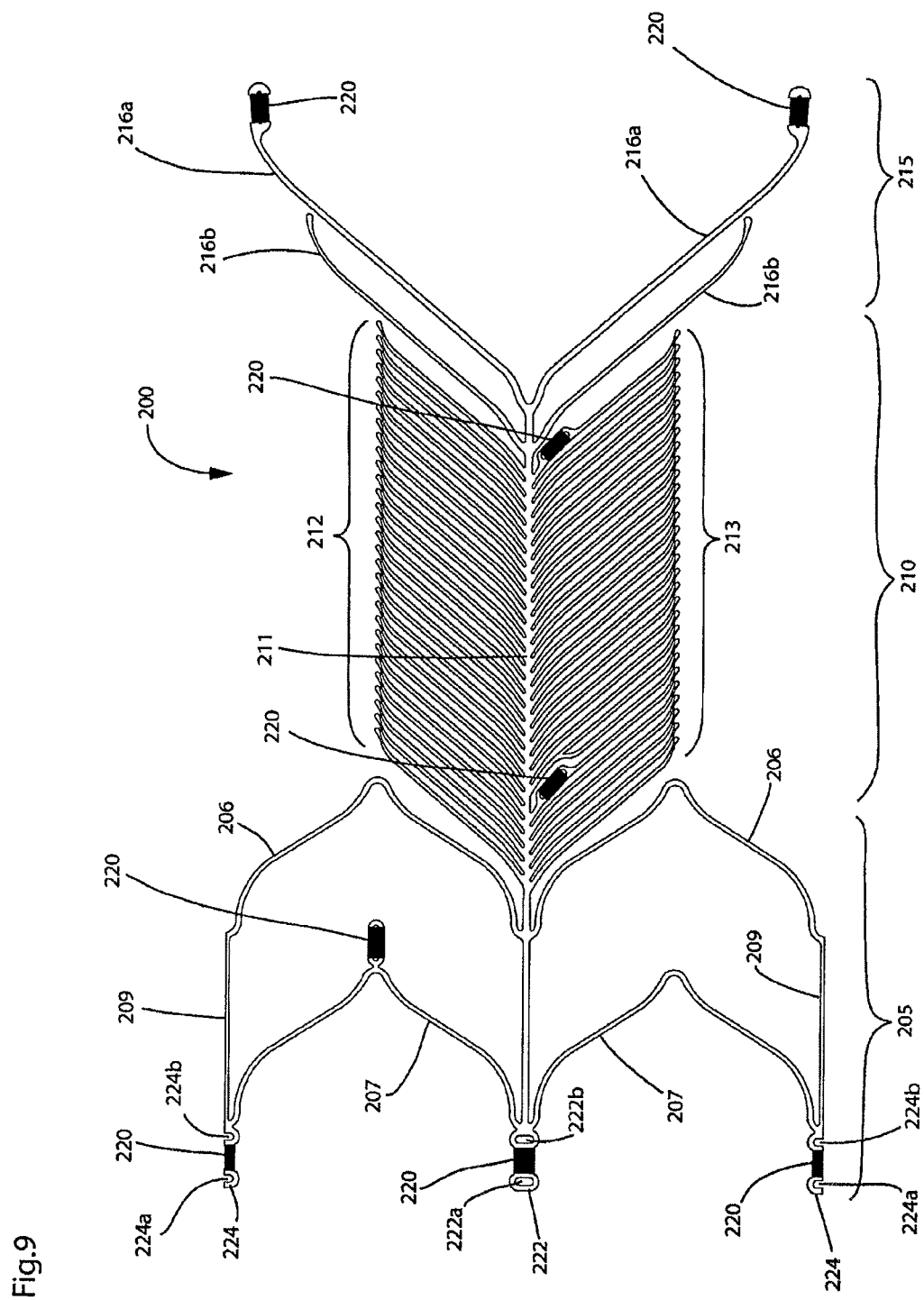
FIG. 9 illustrates a two-dimensional representation of a second embodiment of the present endovascular prosthesis.
Figure 10:
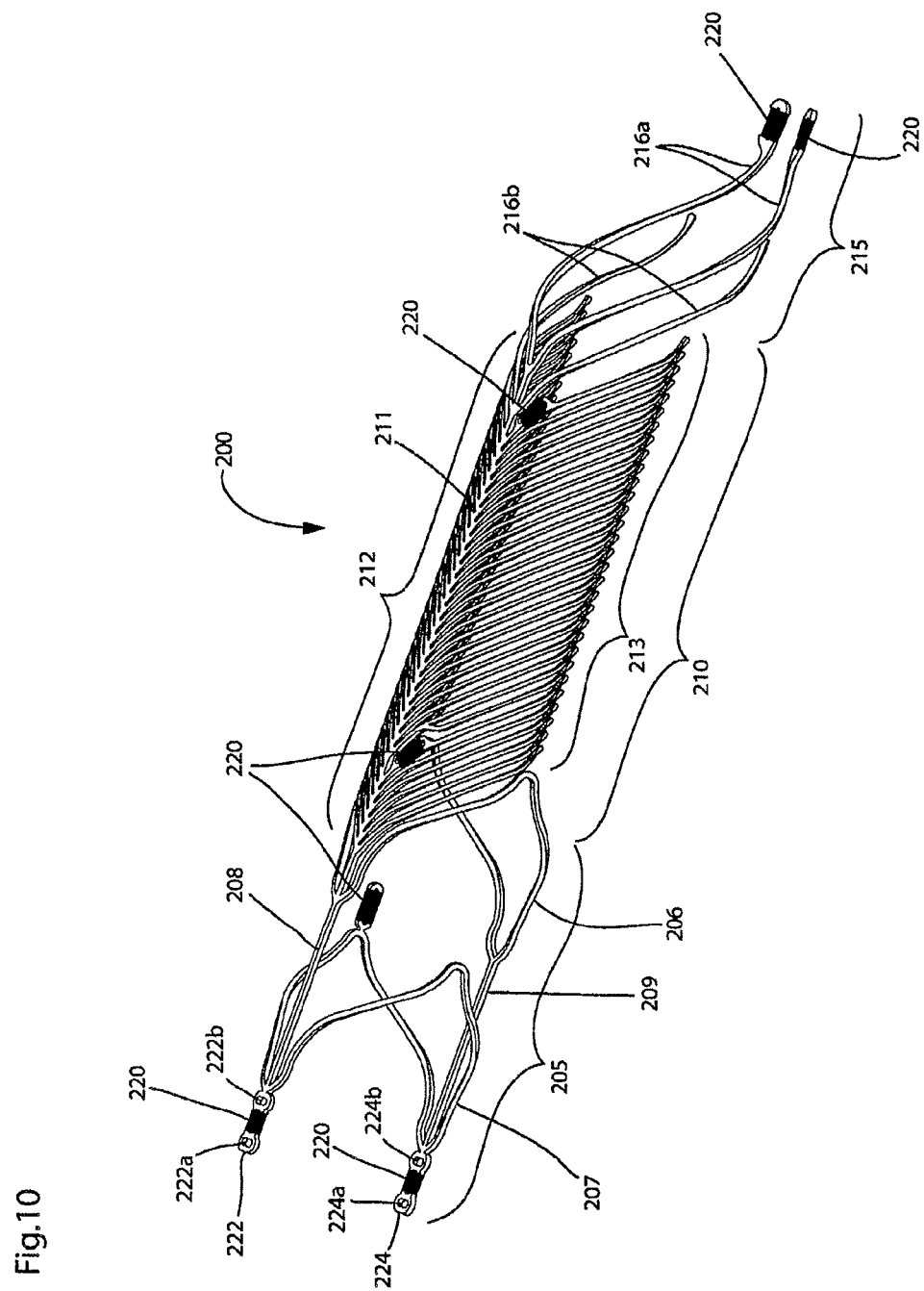
FIG. 10 illustrates a perspective view of the endovascular prosthesis illustrated in FIG. 9.

With reference to FIGS. 9 and 10, there is illustrated an endovascular prosthesis 200. Endovascular prosthesis 200 is similar to endovascular prosthesis 100 illustrated in FIGS. 1-2 with the following exceptions:

single closed loop 116 in loop portion 115 of endovascular prosthesis 100 has been replaced with a pair of split loop portions 216a,216b;

the disposition of radioopaque markers 220 in endovascular prosthesis 200 differs from the disposition of radioopaque markers 120 in endovascular prosthesis 100;

the design of the individual ribs in leaf portion 210 of endovascular prosthesis 200 has been slightly modified with respect to the rib portions in leaf portion 110 of endovascular prosthesis 100;

the rib portions in rows 212,213 of endovascular prosthesis 200 are more closely spaced than in endovascular prosthesis 100; and loops 222 and 224 have been modified for attachment to the delivery system.

The use of split loops 216a,216b provides improved apposition of endovascular prosthesis 200. A single loop 116 as used in endovascular prosthesis 100 can protrude into the lumen of the artery if the single loop is oversized relative to the size of the artery. The provision of pair of split loops 216a,216b allows for overlap of each loop in a given pair while avoiding bending into the lumen of the artery. The addition of radiopaque markers in this embodiment facilitates visualization by the clinician of the location of the extremities of the endovascular prosthesis 200. The provision of radiopaque markers 220 in expansible portion 205 as illustrated facilitates visualization of one end the end of prosthesis 200 while the provision of radiopaque markers 220 in loop portion 215 as illustrated facilitates visualization of one the other end of prosthesis 200.

Furthermore, having two markers near the spine of the leaf and depicting the length of the occlusive length of leaf allows the clinician the ability to evaluate whether or not the leaf length relative to the aneurismal opening 17 is adequate.

As can be seen, loop 222 comprises a pair of apertures 222a,222b. Similarly, loop 224 comprises a pair of apertures 224a,224b.

Figure 11:
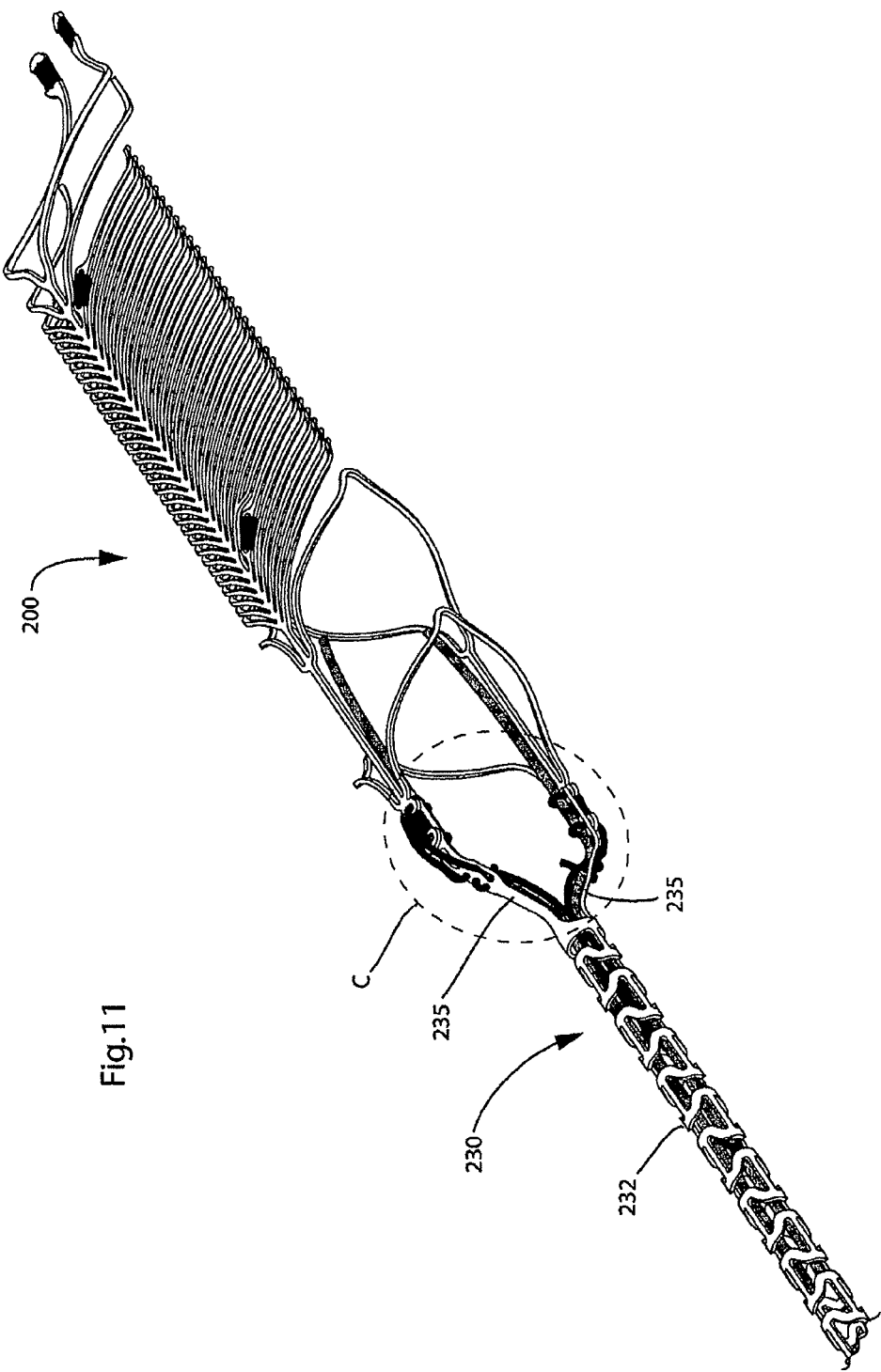
FIG. 11 illustrates a perspective view of the endovascular prosthesis illustrated in FIGS. 9-10 coupled to a delivery device.
Figure 12:
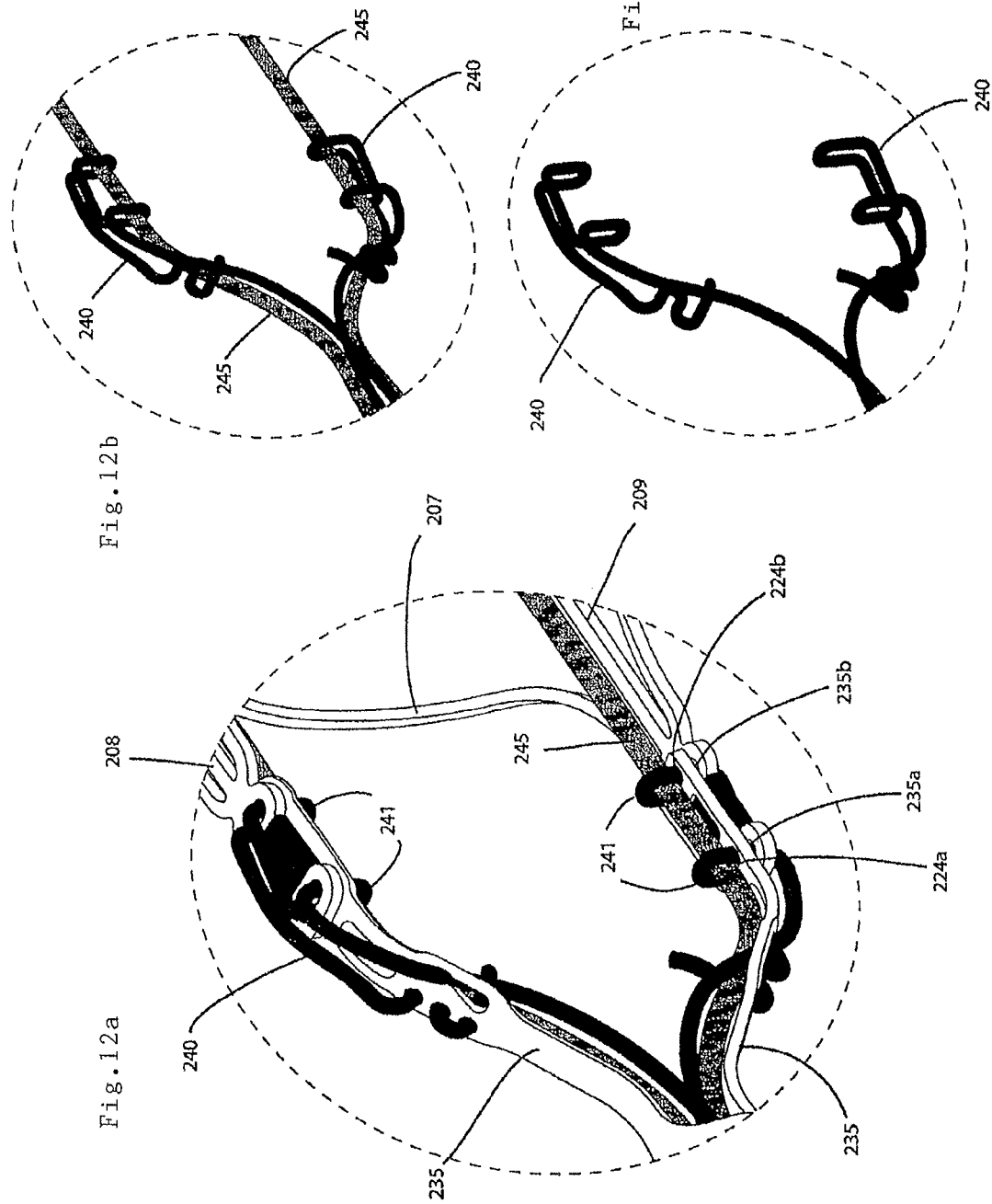
FIGS. 12(a)-12(c) illustrate details of how the endovascular prosthesis illustrated in FIGS. 9-11 is coupled to the delivery device.

With reference to FIG. 11, endovascular prosthesis 200 is attached to a delivery device 230. As can be seen, delivery device 230 comprises a porous tube 232. A pair of arms 235 is provided at the distal end of porous tube 232. FIG. 12(*a*) provides an enlarged view of region C of FIG. 11. As can be seen, each arm 235 has a pair of apertures 235a,235b. Aperture 235a of arm 235 is aligned with aperture 222a or 224a of loops 222 or 224, respectively. Similarly, aperture 235b is aligned with apertures 222b or 224b of loops 222 or 224, respectively. A loop wire 240 is then passed through these aligned loops to create a pair of wire loops 241. Loop wire 240 may be a single wire for each of arms 235 or it may be a pair of independent wires. A release wire 245 is then fed through loops 241. This can be seen more clearly with reference to FIG. 12(*b*) which illustrates the arrangement of loop wire 240 and release wire 245 without the detail of endovascular prosthesis 200 or delivery device 230. FIG. 12(*c*) shows the orientation of loop wire 240 on its own.

Endovascular prosthesis 200 may be navigated to an aneurysm in the same manner as described above with reference to endovascular prosthesis 100. Thus, endovascular prosthesis 200 also has a beneficial feature of being able to be sheathed, unsheathed, re-sheathed, etc. as was the case for endovascular prosthesis 100.

When endovascular prosthesis 200 is positioned correctly. It can be detached from delivery device 230 by sequentially retracting release wire 245 and then retracting loop wire 240. As will be appreciated by those of skill in the art, once release wire 245 is retracted, loops 241 are free to be retracted from the apertures in loops 222,224 and the apertures in arms 235. Once loops 241 have been retracted in this manner, endovascular prosthesis 200 will detach from arms 235 of delivery device 230.

Figure 13:
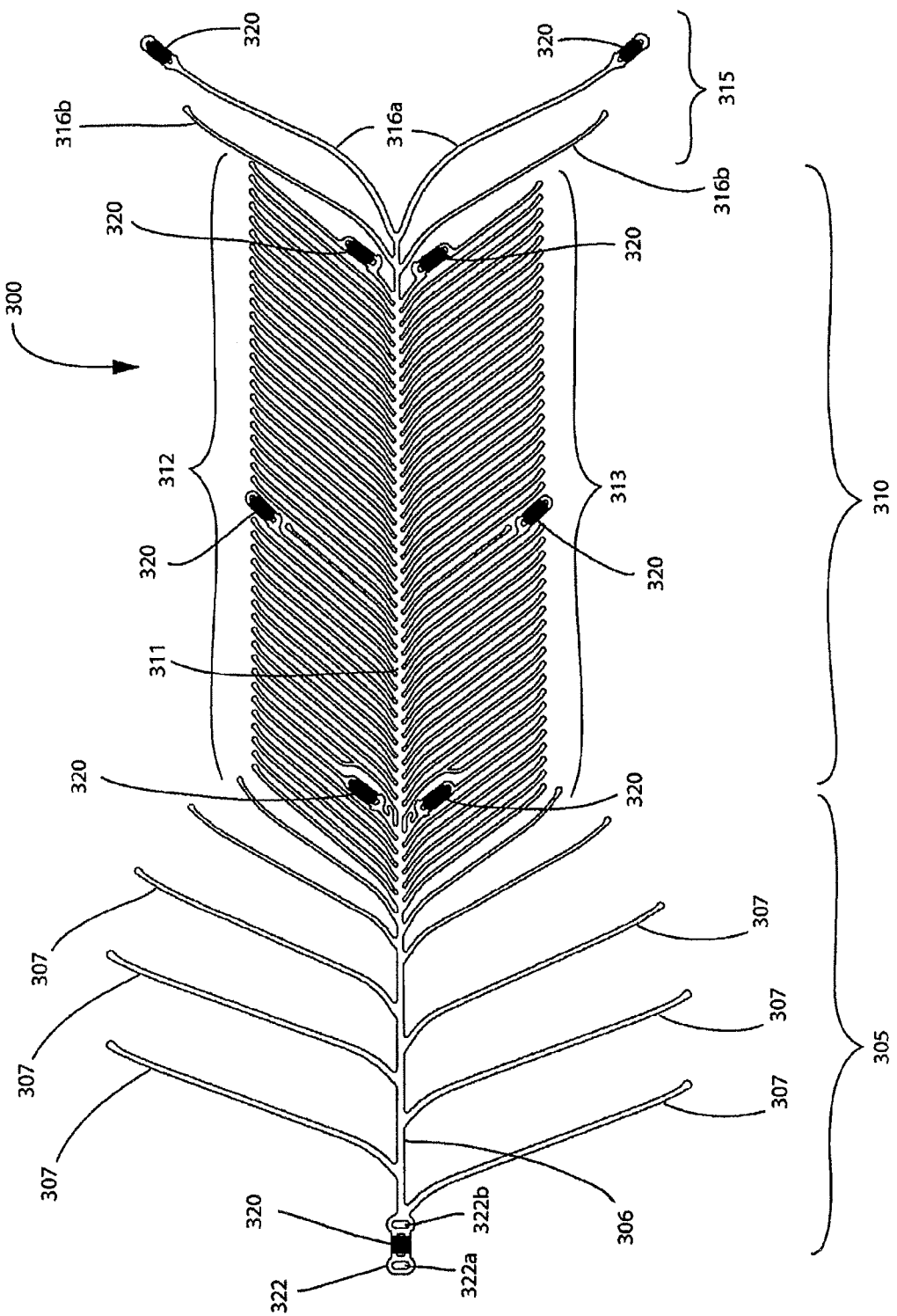
FIG. 13 illustrates a two-dimensional representation of a third embodiment of the present endovascular prosthesis.
Figure 14:
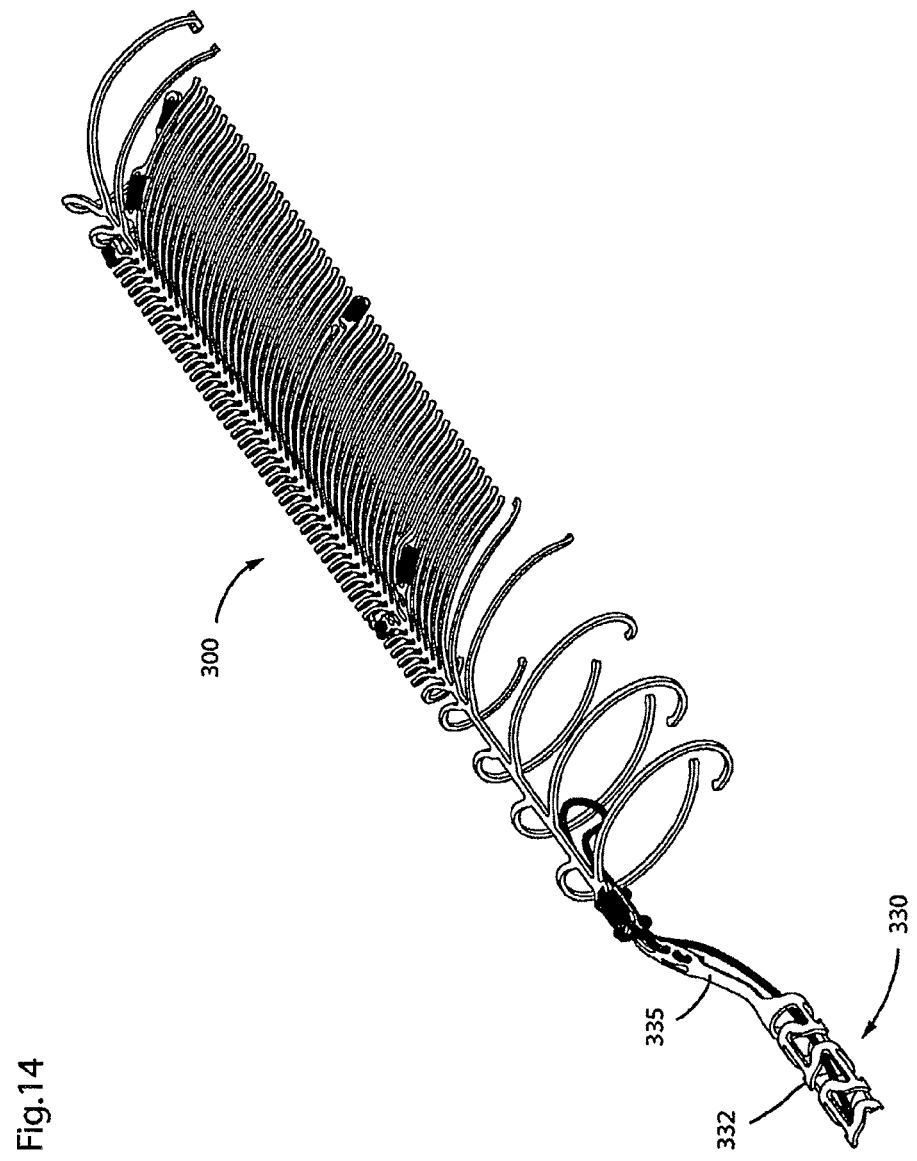
FIG. 14 illustrates a perspective view of the endovascular prosthesis illustrated in FIG. 13 as it is coupled to a delivery device.

With reference to FIGS. 13 and 14, there is illustrated an endovascular prosthesis 300. Endovascular prosthesis 300 is similar to endovascular prosthesis 200 described above with the exception that expansible portion 305 has been modified. Specifically, expansible portion 305 comprises an anchor spine 306 with a series of anchor ribs 307 disposed on opposite sides of anchor spine 306.

The other modification made to endovascular prosthesis 300 is the provision of a single loop 322 comprising a pair of apertures 322a,322b for connection to a delivery device.

The advantages of endovascular prosthesis 300 compared with endovascular prosthesis 200 include:

a single attachment connection between the prosthesis and the delivery device compared to two connections for endovascular prosthesis 200 (and endovascular prosthesis 100); and addition of radioopaque markers near the rib tips near the middle of the leaf portion, which are generally circumferentially orthogonal to the markers close to the spine portion of the leaf portion—these circumferentially orthogonal markers help the clinician to evaluate the rotational position of the device radiographically.

With particular reference to FIGS. 14 and 15, there is illustrated endovascular prosthesis device 300 connected to a delivery device 330 having a porous tube 332. Disposed at the end of porous tube 332 is a single arm 335. Arm 335 comprises a pair of apertures that, during manufacture, can be aligned with apertures 322a,322b of loop 322 of endovascular prosthesis 300. After these apertures are aligned during manufacturing, a single loop/release wire 345 is fed through the aligned apertures to provide a pair of loops 341. The same loop/release wire 345 is then fed back on itself through loops 341 as shown in FIGS. 15(*a*), (*b*), (*c*) and (*d*) which provide various details of how single loop/release wire 345 is positioned. As shown, the end of single loop/release wire 345 is permanently affixed to arm 335.

Endovascular prosthesis 300 may be delivered to a target aneurysm in the same manner as described above with reference to endovascular prosthesis 100 and endovascular prosthesis 200. Once endovascular prosthesis is in the correct position, it may be detached from delivery device 330 by retracting loop/release wire 345. Initial retraction of loop/release wire 345 removes it from loops 341. Continued retraction of loop/release wire 345 removes loops 341 from aligned apertures in loop 322 of endovascular prosthesis 300 and arm 335 of delivery device 330. At this point, delivery device 330 may be withdrawn leaving endovascular prosthesis 300 in place.

The endovascular prosthesis described above with reference to FIGS. 1-15 is particularly well suited for occlusion of a so-called sidewall aneurysm. Occasionally, the target aneurysm is located at an intersection of a bifurcated artery such as the distal basilar artery described above—such a target aneurysm is generally more difficult to treat than a sidewall aneurysm. For treatment of such a target aneurysm, it is preferred to further modify the endovascular prosthesis described above with reference to FIG. 115.

Thus, with reference to FIGS. 16-17, there is illustrated an endovascular prosthesis 400 that is particularly well suited for treatment of an aneurysm located in a bifurcated artery. As can be seen, endovascular prosthesis 400 is similar to endovascular prosthesis 100 described above with reference to FIGS. 1-2 with the following modifications:

- expansible portion 405 (including circumferential rings 406,407 and struts 408,409) have been translated to the opposite end of the spine 411 so that spine 411 is connected to a peak of circumferential ring 406 (cf. spine 111 in endovascular prosthesis 100 which is connected to a valley of circumferential ring 106)—this feature facilitates delivery of endovascular prosthesis 400 into either a straight or bifurcated body passageway;
- detachment loops 422,424 are located on opposed ends of endovascular prosthesis 400 (cf. loops 122,124 located on expansible portion 105 of endovascular prosthesis 100);
- there is no loop portion in the proximal end of endovascular prosthesis 400 as there is an endovascular prosthesis 100 (cf. loop portion 115); and
- a single attachment portion 424 is provided at a proximal end of spine 411 of endovascular prosthesis 400.

With reference to FIGS. 18-21, there is illustrated delivery and deployment of endovascular prosthesis 400 in a bifurcated artery 50. As can be seen, bifurcated artery 50 comprises an aneurysm 55 having an aneurysmal opening 57.

Of particular note in FIGS. 18-21 is the general manner in which endovascular prosthesis is oriented during delivery and deployment. Specifically, when any of endovascular prosthesis 100,200,300 described above is delivered to a sidewall aneurysm, delivery is accomplished by orienting the expansible portion (105,205,305) such that it is proximal to the clinician whereas the loop portion (115,215,315) is oriented distally with respect to the clinician thus exiting delivery catheter 440 first. In contrast, when delivering endovascular prosthesis 400 to bifurcated artery 50, expansible portion 405 is oriented distally with respect to the clinician whereas loop 424 (at the opposed end of endovascular prosthesis with respect to expansible portion 405) is oriented proximally with respect to the clinician thus exiting delivery catheter 440 last.

With reference to FIG. 18(*a*), a guidewire 66 is inserted and passed through a first branch 51 of bifurcated artery 50. Next, with reference to FIG. 18(*b*), delivery catheter/sheath 440 is passed over guidewire 66 into first branch 51 of bifurcated artery 50.

Next, with reference to FIG. 18(*c*), guidewire 66 is withdrawn from first branch 51 of bifurcated artery 50. With reference to FIG. 18(*d*) endovascular prosthesis 400 attached to delivery device 430 is fed through delivery catheter/sheath 440 until endovascular prosthesis 400 is positioned in first branch 51 of bifurcated artery 50.

With reference to FIG. 18(*e*) delivery catheter/sheath 440 is thereafter retracted: this results in initial deployment of expansible portion 405 of endovascular prosthesis 400. If the physician is not satisfied with this initial deployment of expansible portion 405 of endovascular prosthesis 400, he/she may re-sheath endovascular prosthesis 400 in an attempt to reposition it within first branch 51 of bifurcated artery 50.

Once the physician is satisfied with the initial deployment of endovascular prosthesis 400, delivery catheter/sheath 440 is further retracted exposing the proximal portion of endovascular prosthesis 400—see FIG. 18(*f*).

Figure 19:
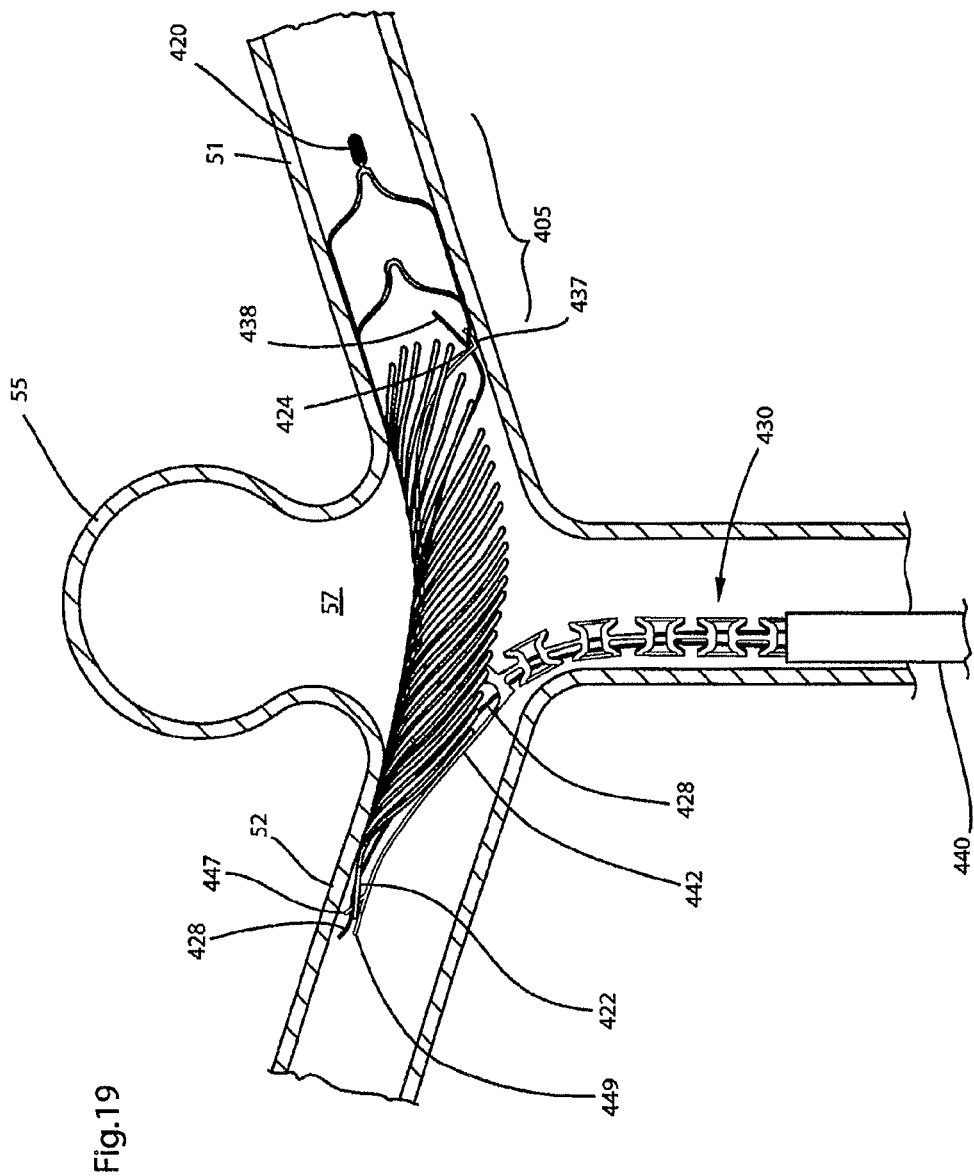

With reference to FIG. 19, delivery device 430 is further extended as shown in FIG. 19. This further extension naturally progresses into a second branch 52 of bifurcated artery 50 due to the initial deployment of endovascular prosthesis 400.

Figure 21:
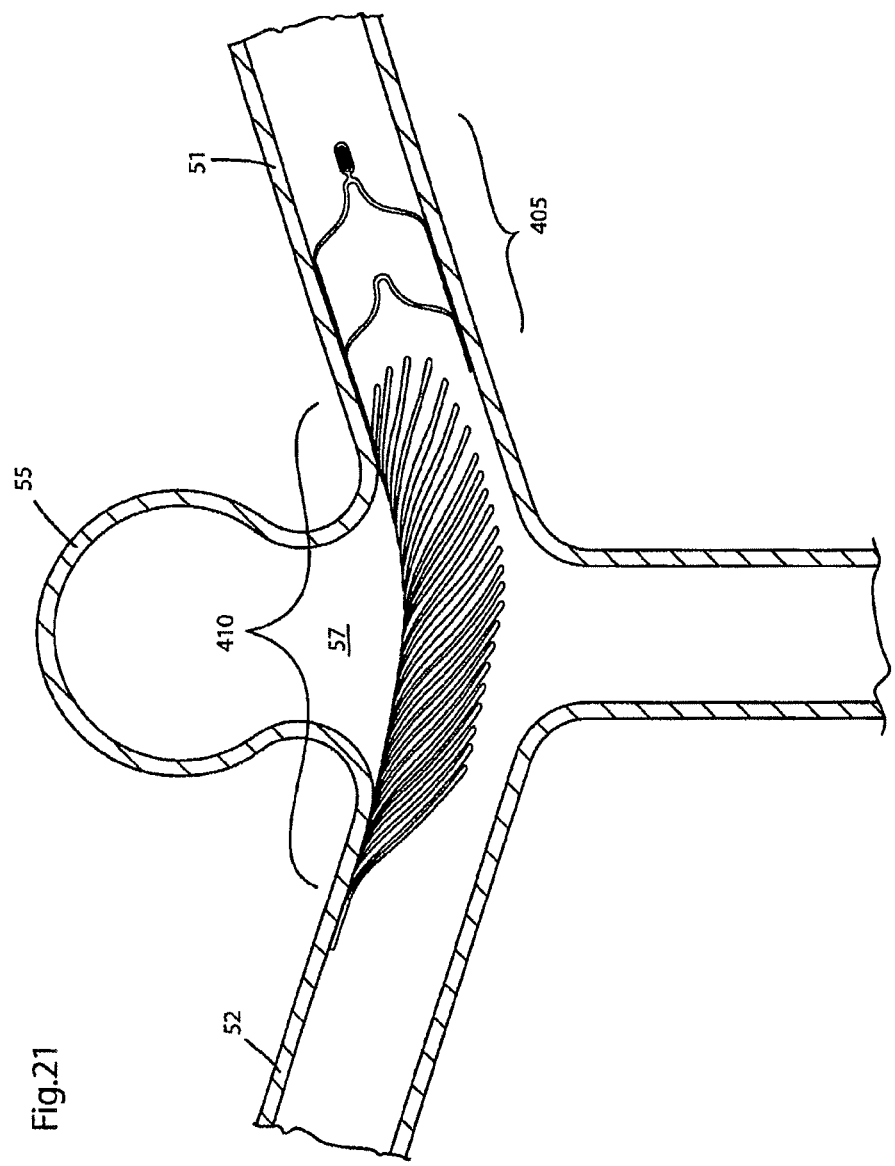

Once it has been determined that endovascular prosthesis 400 is in the correct position, delivery device 430 is detached from endovascular prosthesis 400 in the manner to be discussed below. This allows for withdrawal of delivery catheter 440 and delivery device 430 resulting in final deployment of endovascular prosthesis 400 as shown in FIG. 21. In this final deployed configuration, leaf portion 410 of endovascular prosthesis 400 occludes aneurysmal opening 57 of aneurysm 55.

Figure 25:
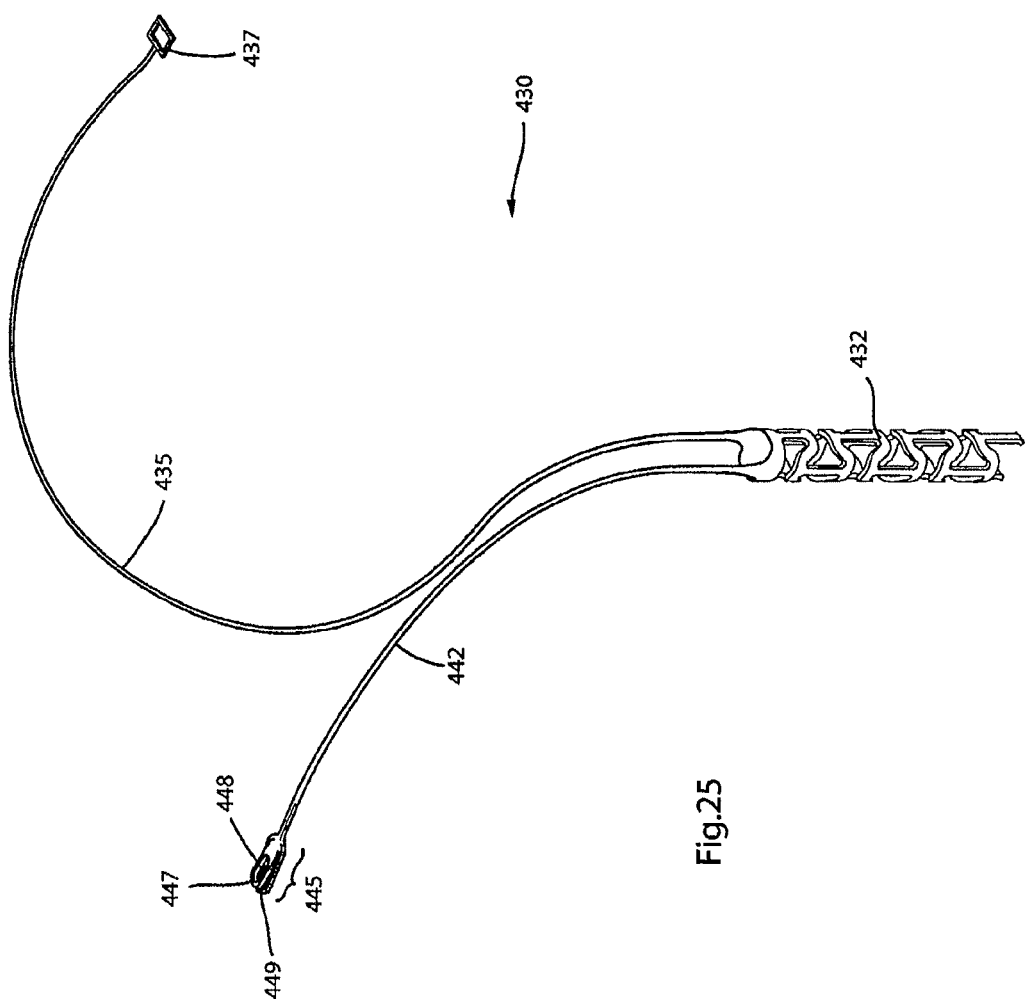
FIG. 25 illustrates a perspective view of a portion of the delivery device used to deliver the endovascular prosthesis illustrated in FIGS. 16-24.

With reference to FIG. 25, there is illustrated a delivery device 430 for delivery of endovascular prosthesis 400. Delivery device 430 comprises a porous surface 432 similar to the one described above with reference to endovascular prosthesis 100,200,300. Delivery device 430 further comprises a first arm 435 having a square aperture 437 and a second arm 442 having a cleat/buckle attachment 445. Cleat/buckle attachment 445 comprises a finger portion 447 having an aperture 448. Finger portion 447 is movable with respect to a protector portion 449 of cleat/buckle attachment 445. Protector portion 449 of cleat/buckle attachment 445 protects against snagging of loop 424 during refraction of endovascular prosthesis 400.

With reference to FIGS. 22-24, there is illustrated further detail on attachment of arm 435 of delivery device 430 to loop portion 424 of expansible portion 405 of endovascular prosthesis 400. Thus, loop portion 424 is inserted in square aperture 437 and a wire 438 is inserted through loop portion 424 so as to secure loop portion 424 with respect to square aperture 437—see FIG. 22. Once endovascular prosthesis is in the correct position and the clinician desires to detach delivery device 430 from endovascular prosthesis 400, wire 438 is retracted as shown in FIG. 23. This allows arm 435 to be separated from loop portion 424 of endovascular prosthesis 400 as shown in FIG. 24.

Figure 20:
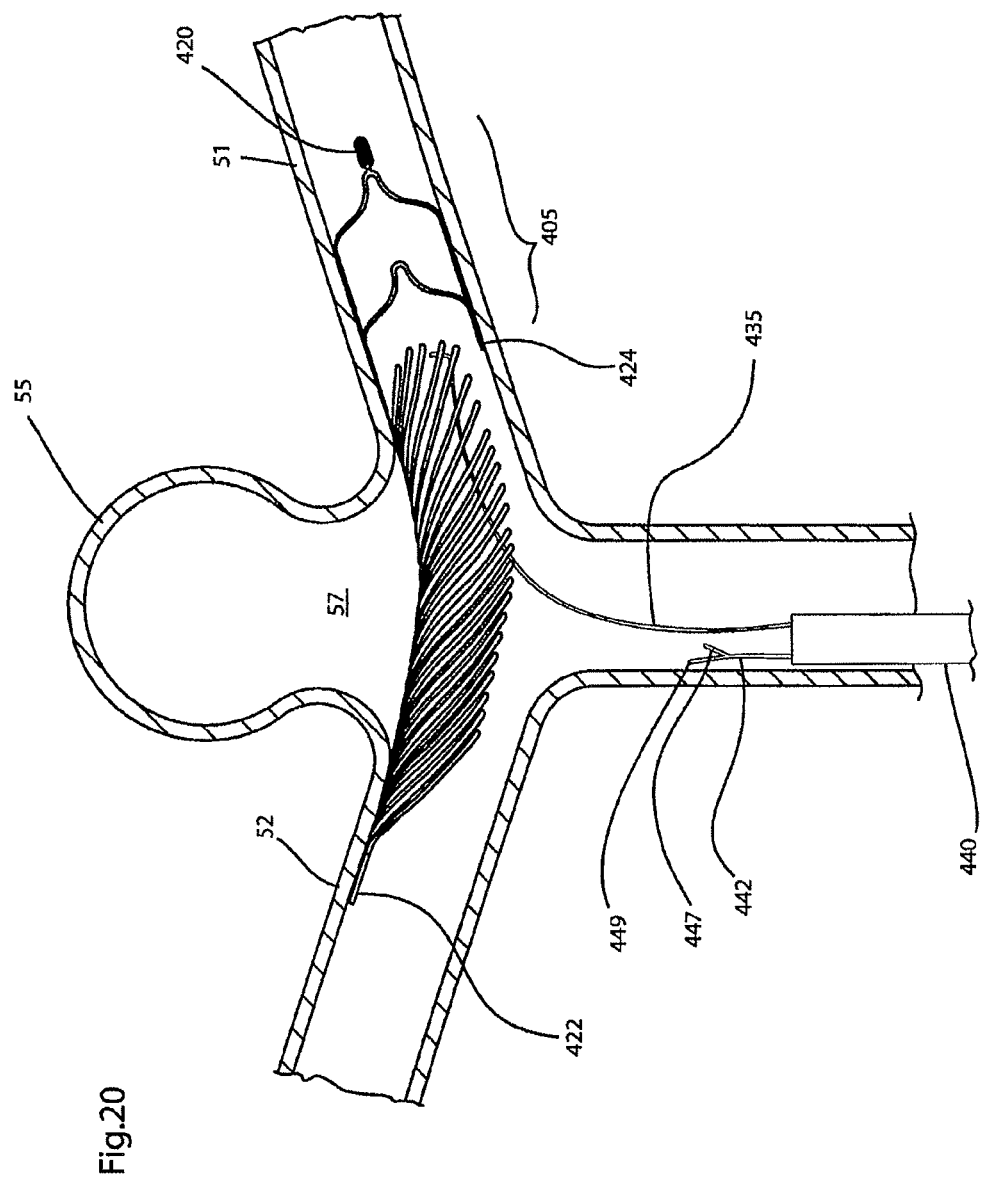
Figure 27:
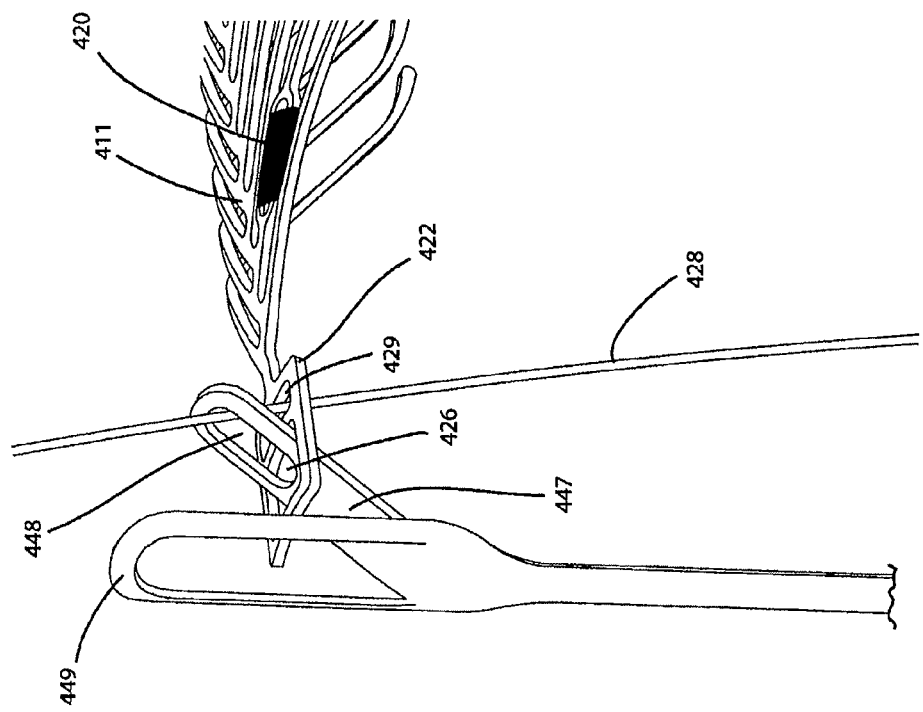
FIGS. 26-27 illustrate an enlarged view of the portion of the delivery device illustrated in FIG. 25 and how it is coupled to an opposite end (cf.
Figure 26:
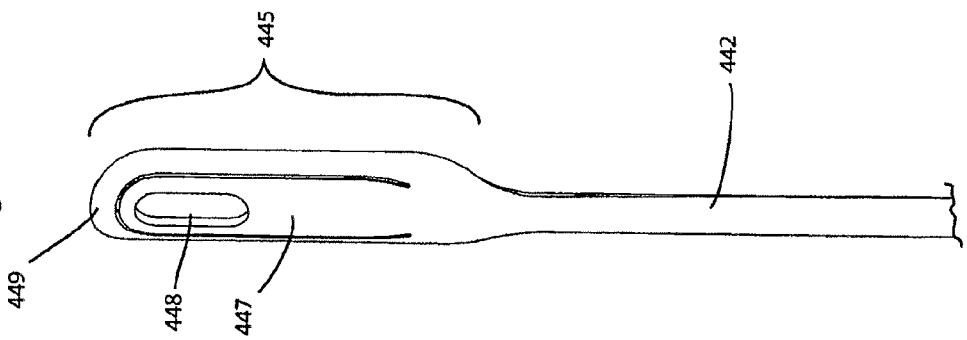

With reference to FIGS. 26 and 27, there is illustrated further detail of attachment of attachment portion 422 of endovascular prosthesis 400 to cleat/buckle attachment 445 of arm 442 of delivery device 430—for ease of understanding the illustration has been styled outside the vasculature (cf. FIG. 20). Thus, finger portion 447 of cleat/buckle attachment 445 is inserted in a first aperture 426 of attachment portion 422. A wire 428 is inserted through a second aperture 429 of attachment portion 422 such that it also passes through aperture portion 448 of finger portion 447 of cleat buckle attachment 445—see FIG. 27. This arrangement serves to secure attachment portion 422 of endovascular prosthesis 400 with respect to cleat/buckle attachment 445 of delivery device 430.

When endovascular prosthesis 400 is in the correct position and the clinician wishes to detach endovascular prosthesis 400 from delivery device 430, the clinician retracts wire 428 from apertures 429,448. This allows finger portion 447 to be able to be retracted from aperture 426 of attachment portion 422 thereby allowing detachment of that portion of endovascular prosthesis 400 from delivery device 430.

At this point, delivery device 430 is detached from endovascular prosthesis 400 and the former may be fully refracted from the patient through delivery catheter/sheath 440 as shown in FIG. 20. The final deployment of endovascular prosthesis 400 is illustrated in FIG. 21.

With reference to FIGS. 28-35, there is illustrated an endovascular prosthesis 500 that is particularly well suited for treatment of an aneurysm located in a bifurcated artery. As can be seen, endovascular prosthesis 500 is similar to endovascular prosthesis 400 described above with reference to FIGS. 16-17 with the following general modifications:
  the provision of arms 519;
  the single radioopaque marker 420 in endovascular prosthesis 400 has been replaced by a trio of radioopaque markers 520a,520b,520c;
  the arrangement of radioopaque markers 520 in the rows 512,513 of rib portions has been altered;
  single attachment portion 424 provided at the end of spine 411 of endovascular prosthesis 400 has been replaced by a pair of arms 519 at the end of which is an attachment portion 524 comprising a pair of apertures 526,529.

A number of technical effects accrue from these modifications. The additional radiopaque markers provide the clinician with information about the location in the patient of the proximal and distal extremities of the endovascular prosthesis 500. In endovascular prosthesis 400, the radioopaque markers were disposed along the same side of the spine portion of the prosthesis. In contrast, in endovascular prosthesis 500, the radioopaque markers alternate along the spine portion and the most proximal radioopaque marker is centred with the spine. Pair of arms 519 in endovascular prosthesis 500 serve to urge the spine and rib portions toward the aneurysmal opening and provide support to the spine and rib portions to urge them against the artery wall. Furthermore, pair of arms 519 replace the function of second arm 442 of the delivery device used in endovascular prosthesis 400.

Figure 30:
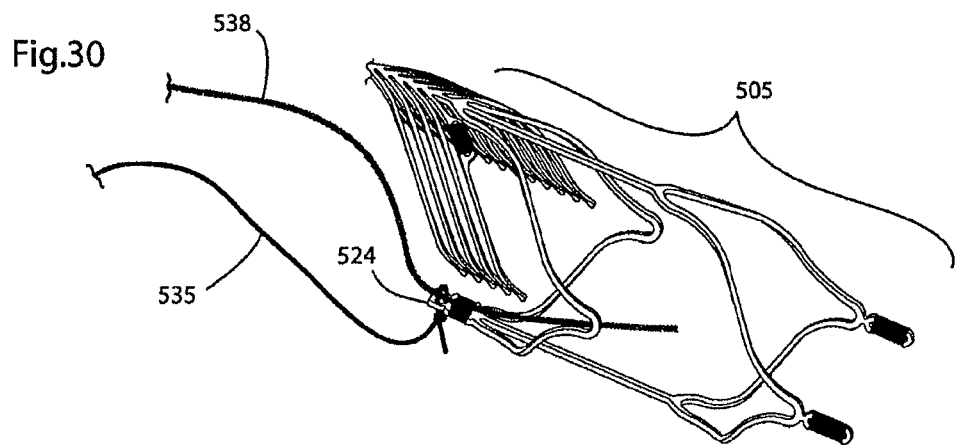
FIGS. 30-32 illustrate, in a step-wise manner, release of the endovascular prosthesis illustrated in FIGS. 28-29 from its delivery device.
Figure 31:
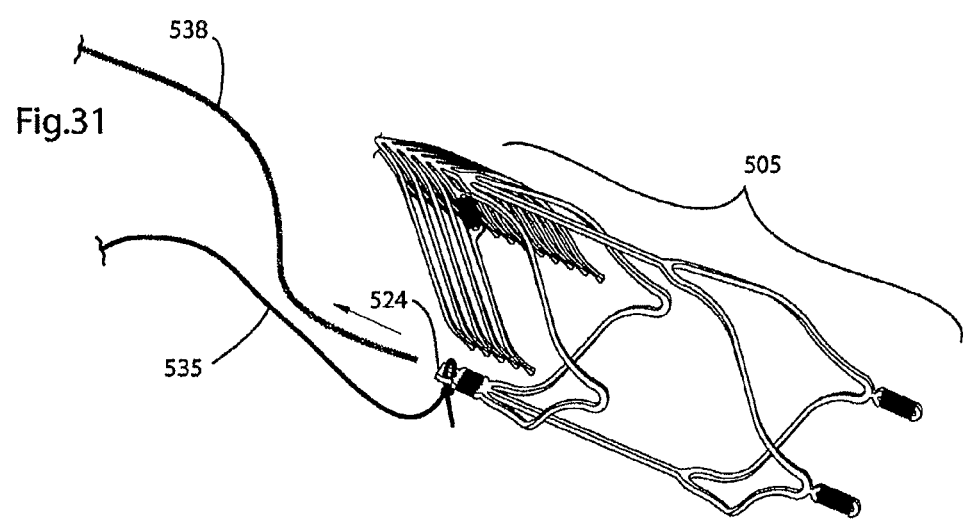
Figure 32:
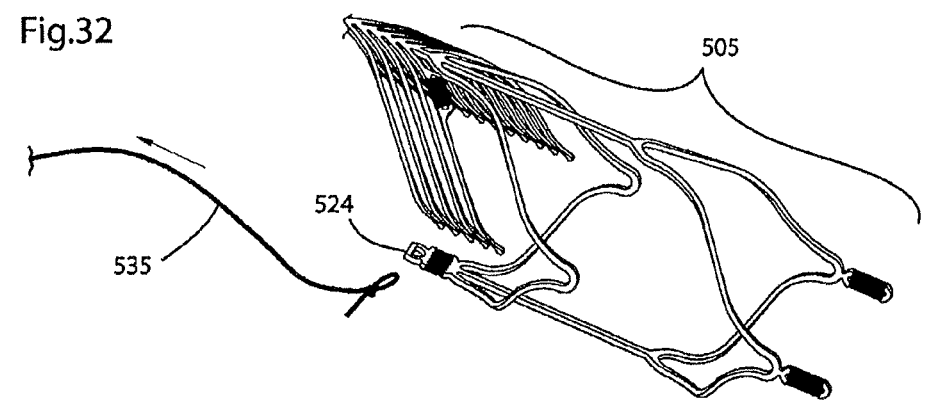

With reference to FIGS. 30-35, there is illustrated attachment of endovascular prosthesis 500 to a delivery device 530 which is similar to delivery device 430 described above. One difference is that first arm 435 of delivery device 430 has been replaced with a first wire portion 535 which is fed into loop portion 524 of expansible portion 505. A wire 538 is fed through wire portion 535 as shown in FIG. 30 which illustrates attachment of delivery device 530 to expansible portion 505. When it is desired to detach wire portion 535 form expansible portion 505, wire 538 is retracted which allows wire portion 535 to disengage from loop portion 524 of expansible portion 505—see FIGS. 31 and 32.

Figure 33:
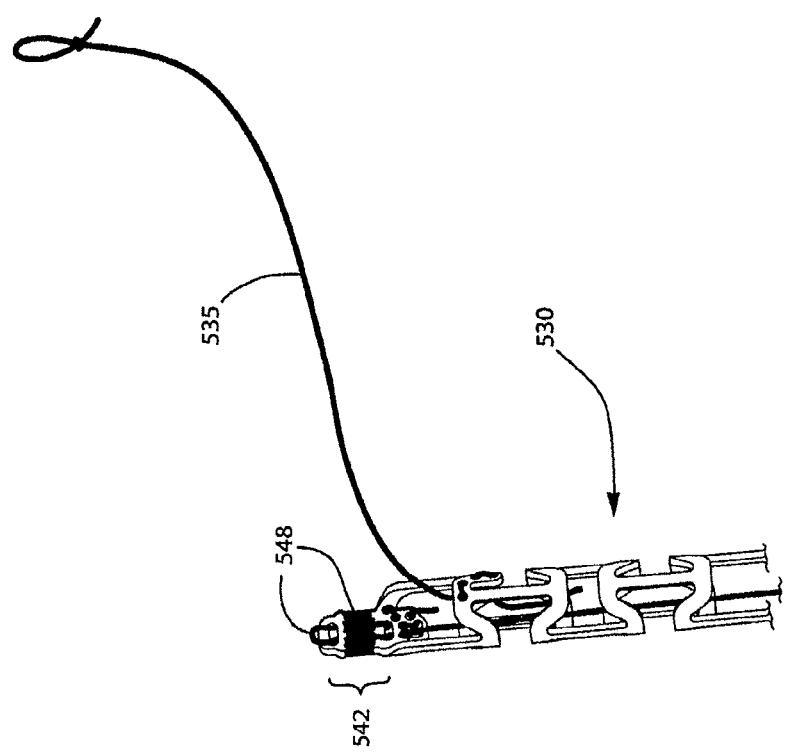

With reference to FIG. 33, there is shown additional detail on delivery device 530. In essence, arms 435,442 used in endovascular prosthesis 400 have been omitted. Specifically, arm 435 has been replaced with wire portion 535 and arm 442 has been omitted and replaced with a pair of arms 519 in endovascular prosthesis 500—see FIG. 34. The function of arm 442 is replaced by the presence of arms 519 in endovascular prosthesis 500 with the added advantage that the curvature in arms 519 in endovascular prosthesis 500 aid in correct placement of endovascular prosthesis 500 in a bifurcated artery.

As shown, delivery device 530 comprises an attachment portion 542 which is aligned with apertures 526,529 of arms 519 of endovascular prosthesis 500 and secured as a unit by a loop wire 548 and a release wire 528. As shown in FIG. 34, arms 519 of endovascular prosthesis 500 are aligned such that respective apertures 526,529 of each arm 519 are aligned. Loop wire 548 is passed through attachment portion 542 of delivery device 530. A refraction wire 528 is passed through loop wire 548 as shown in FIG. 34 and also as shown in FIG. 35.

Endovascular prosthesis 500 may be delivered using delivery device 530 in a manner similar to that described above in FIGS. 18-21 with reference to endovascular prosthesis 400.

Figure 36:
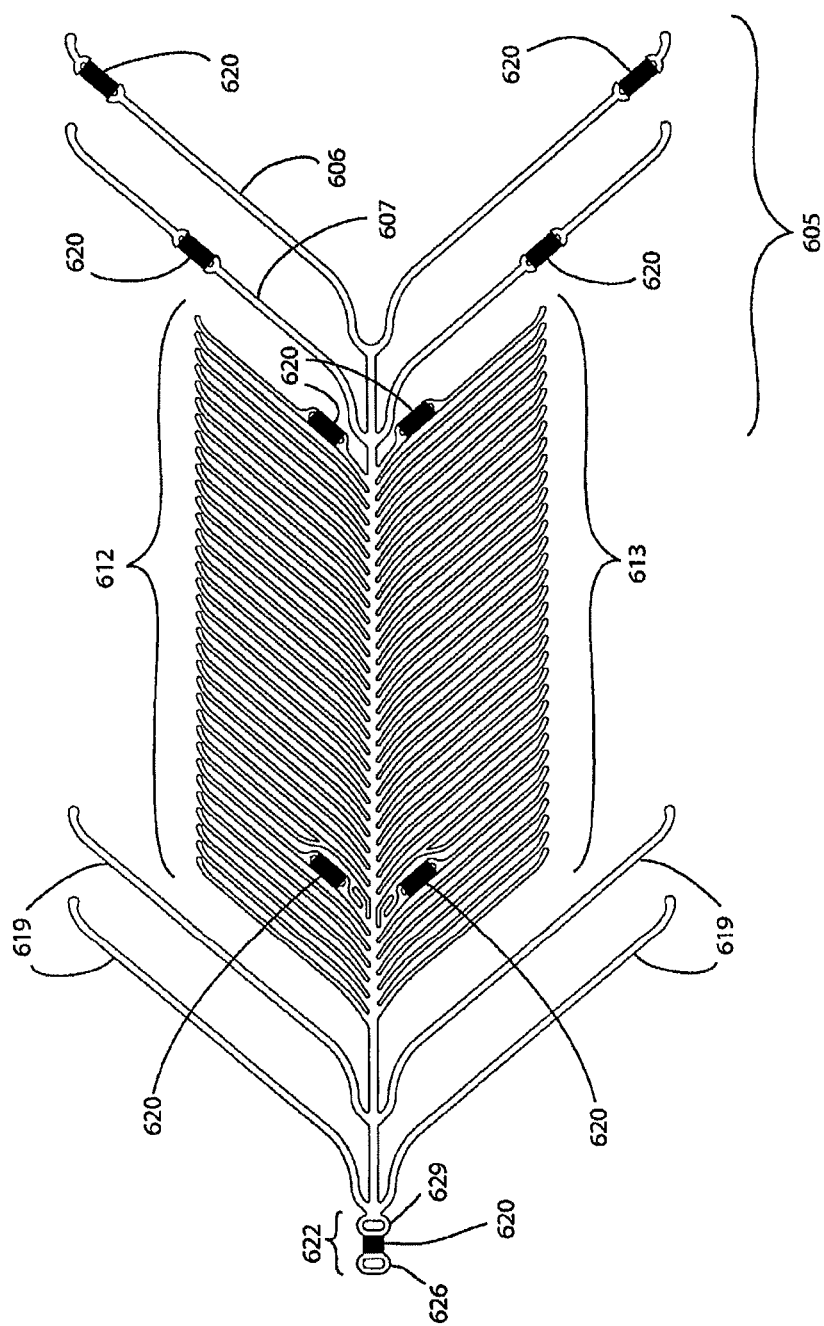
FIG. 36 illustrates a two-dimensional representation of a sixth embodiment of the present endovascular prosthesis.
Figure 37:
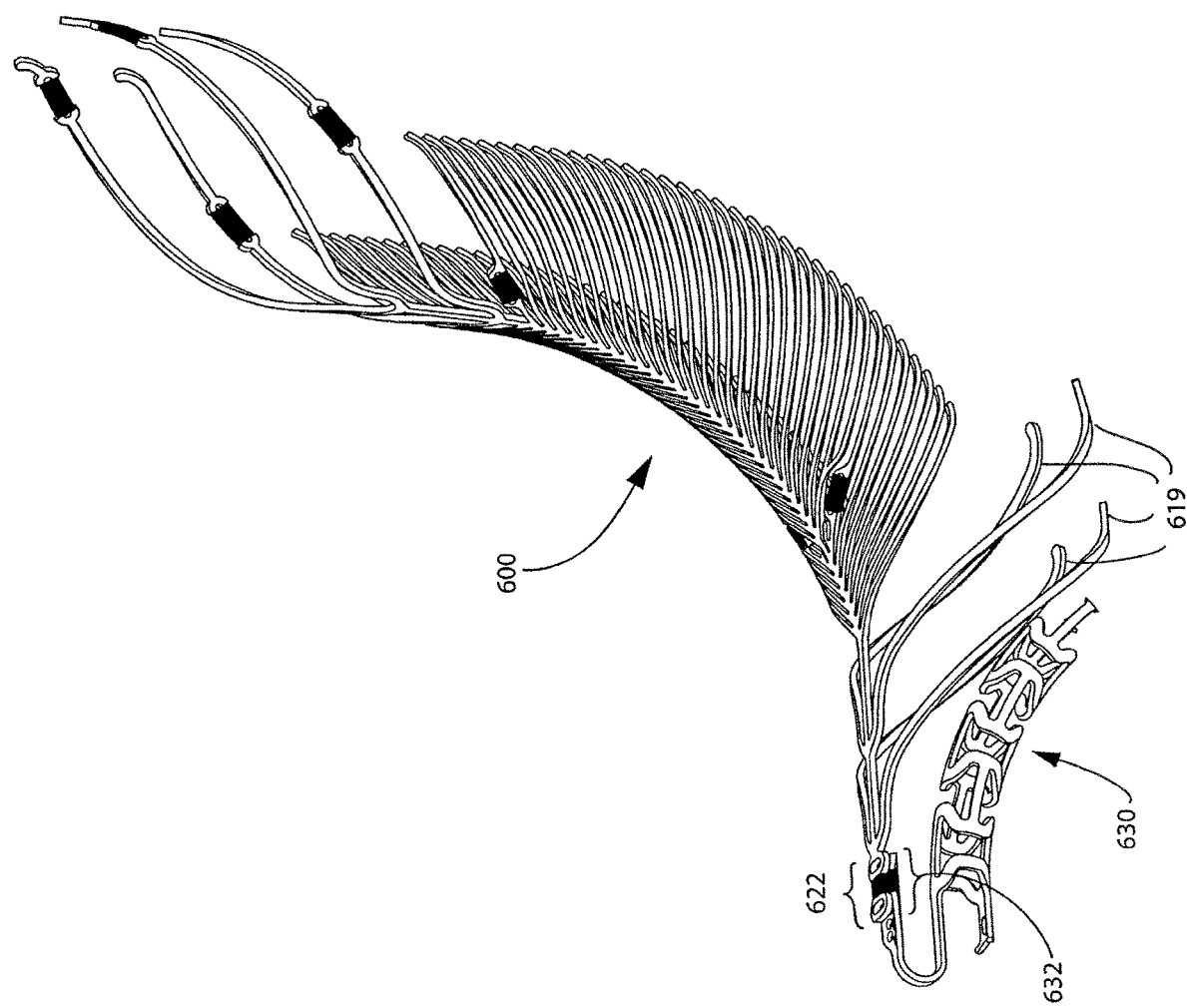
FIG. 37 illustrates a perspective view of the endovascular prosthesis illustrated in FIG. 36 connected to a delivery device therefor.
Figure 39D:
Figure 39A:
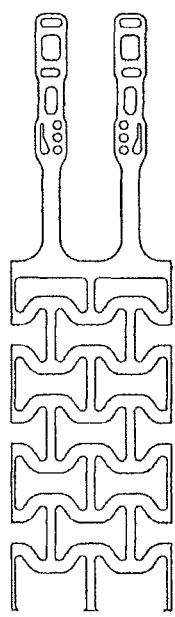
Figure 39B:
Figure 39C:
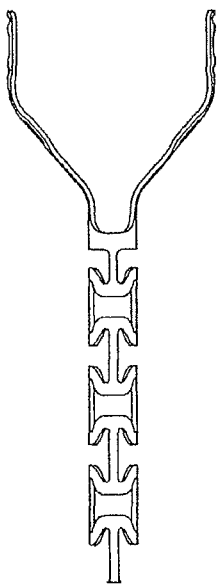
Figure 41:
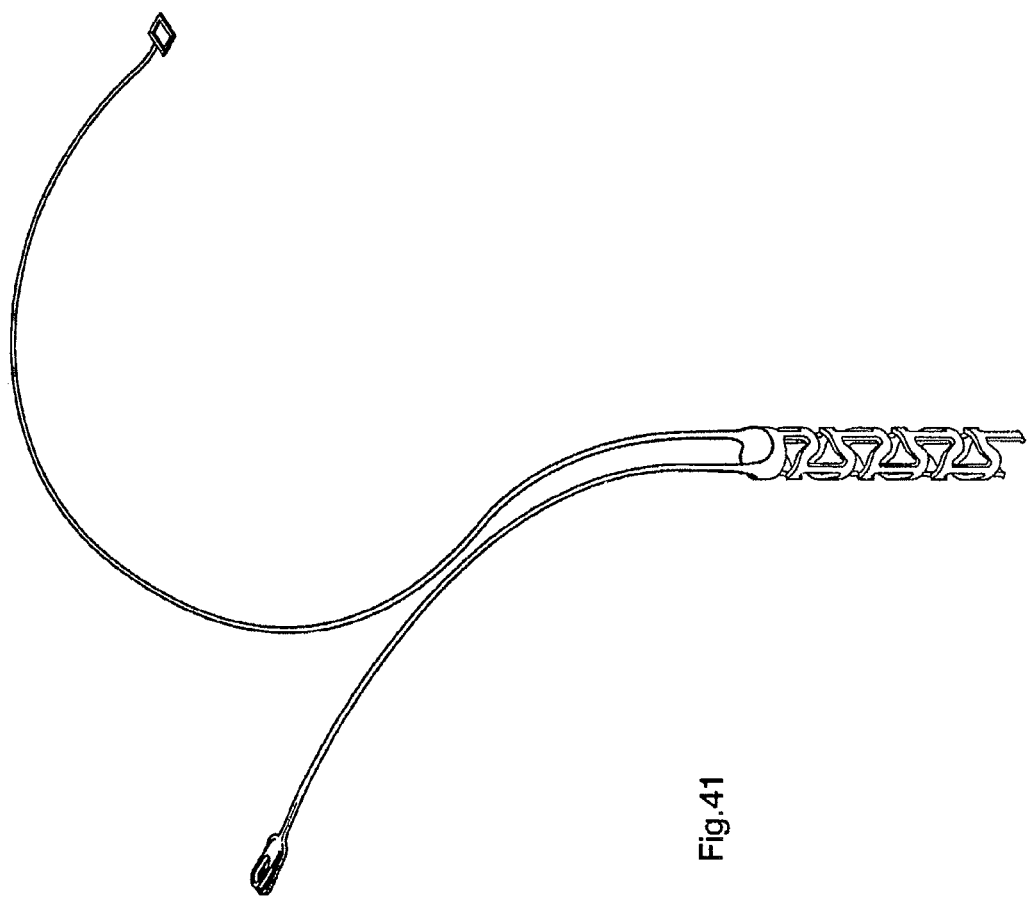
Figure 42C:
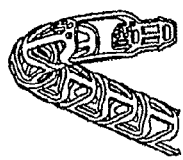
Figure 42A:
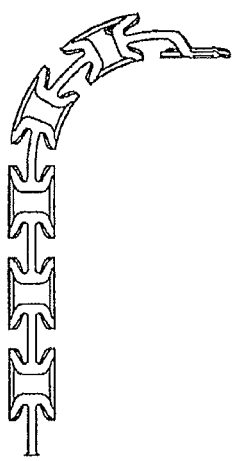
Figure 42B:
Figure 43D:
Figure 43E:
Figure 43A:
Figure 43B:
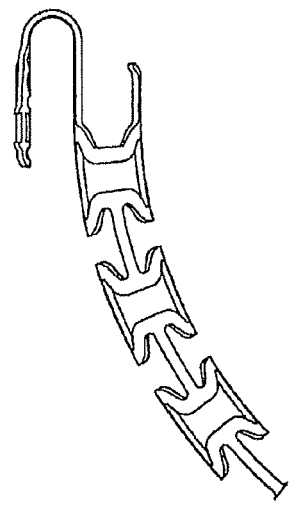
Figure 43C:

With the reference to FIGS. 36 and 37, there is illustrated an endovascular prosthesis 600 that is particularly well suited for treatment of aneurysm located in a bifurcated artery. As can be seen, endovascular prosthesis 600 is similar to endovascular prosthesis 500 described above with reference to FIGS. 28 and 29 with the following general modifications:
  pair of arms 519 in endovascular prosthesis 500 have been replaced with a quartet of arms 619;
  radioopaque markers 620 are arranged differently in endovascular prosthesis 600 then radioopaque markers 520a,520b,520c,520 in endovascular prosthesis 500;
  longitudinal strut 509 has been deleted thereby resulting in element 606,607 being noncircumferential extending (they may be regarded as so-called "split loops"); and
  an element corresponding to attachment point 522 does not exist on endovascular prosthesis 600, because the "expansible portion" has been replaced with ribs or split loops and as such, no longer requires an attachment point.

One of the principle advantages of endovascular prosthesis 600 is that it may be delivered with a delivery device 630 which consists of a single attachment to endovascular prosthesis 600. The provision of arms 619 will improve urging of the spine portion and rib portions against the aneurysmal opening and against the artery wall. This is particularly advantageous since it allows for implantation of endovascular prosthesis in more varied anatomy than endovascular prosthesis 500. If endovascular prosthesis 600 is oversized relative to the target artery, arms 619 will remain against the artery wall and overlap each other, whereas in endovascular prosthesis 500, arms 519 may encroach into the lumen of the artery if the prosthesis were oversized. Similar advantage accrues with reference to elements 606 and 607. Finally, there are radioopaque markers disposed on both sides of the spine portion in endovascular prosthesis 600 compared to the alternating arrangement used in endovascular prosthesis 500—this provides a more detailed description of the leaf spine radiographically which allows for optimal positioning with respect to the aneurysmal opening.

FIG. 37 illustrates connection of endovascular prosthesis 600 to delivery device 630. Specifically, attachment portion 622 of endovascular prosthesis 600 is aligned with an attachment portion 632 of delivery device 630. While the details of connecting endovascular prosthesis 600 to delivery device 630 are not illustrated in FIG. 37, it is preferred to utilize a single loop/release wire as described above with reference to FIGS. 14 and 15 with the proviso that loops 341 are inverted when connecting endovascular prosthesis 600 to delivery device 630.

With reference to FIGS. 38(*i*)-38(*iii*), there are illustrated various views of the distal portion of a endovascular prosthesis delivery device 5. The illustrated distal portion has a porous surface. The remainder of the endovascular prosthesis delivery device (not shown for clarity) is substantially non-porous.

As illustrated, there is an overall increase in porosity of the porous surface of the endovascular prosthesis delivery device 5 moving from a proximal portion of the porous surface to the distal portion of the porous surface (left to right in FIGS. 38(*i*)-(*iii*)).

The present inventors have discovered that a combination of specific dimensions of the porous surface is particularly useful in conferring a highly desirable balance between longitudinal flexibility and sufficient structural integrity (re. torquing ability) to facilitate delivery of an endovascular prosthesis, particularly through tortuous vasculature.

Specifically, with particular reference to FIGS. 38(*a*) and 38(*b*), a functional advantage accruing from a porous surface having the combination of dimensions if it allows for bending of a longitudinal strut 10 in the porous surface until the amount of bending allows for edges 20 of adjacent circumferential rings 25 to contact each other, at which point no further bending (strain) can be applied to longitudinal strut 10. Consequently, there is a limit on the amount of strain that can be placed on longitudinal strut 10, thereby reducing the likelihood of kinking, yield and/or failure of the material used to produce the porous surface of endovascular prosthesis delivery device 5.

With reference to FIGS. 38(*a*)-38(*d*), the dimensions for elements O, P, Q and R appearing in those drawings denote the concurrent transition for all of these elements from one end of the device to the other end:

will be appreciated that endovascular prosthesis delivery device 5 can be used to deliver other types of endovascular prostheses.

FIGS. 38-43 illustrate enlarged views of the distal portions of the various delivery devices described above identified with reference numerals ending in "30". The following is a concordance of the above-described delivery devices and the above-described endovascular prosthesis preferably delivered by that delivery device:

| Figure | Delivery Device | Endovascular Prosthesis |
|---|---|---|
| 38 | 130 | 100 |
| 39(a)-(d) | 230 | 200 |
| 40(a)-(d) | 330 | 300 |
| 41 | 430 | 400 |
| 42(a)-(c) | 530 | 500 |
| 43(a)-(e) | 630 | 600 |

As can be seen in FIGS. 39-43, the porous, tubular portion of each delivery device is very similar but the distal section which is used to attach to the endovascular prosthesis is varied in each embodiment to accommodate the specific type of endovascular prosthesis. In Figures, the distal section which is used to attach the endovascular prosthesis is heat set (e.g., in when the delivery device is constructed from a shape memory alloy such as nitinol) to facilitate delivery of the endovascular prosthesis—this is particularly advantageous when it is desired to deliver the endovascular prosthesis to a bifurcated artery. The point is, a person of ordinary skill in the art, having in hand the present specification will understand that the specific nature of the distal section which is used to attach to the endovascular prosthesis is not specifically restricted. Further, a person of ordinary skill in the art will understand, having this specification in hand, that it may be possible to mix and match certain

| | Dimension (in.) | | | |
|---|---|---|---|---|
| | O | P | Q | R |
| Preferred | 0.0250-0.0010 | 0.0010-0.0450 | 0.0400-0.0050 | 0.0010-0.0500 |
| More preferred | 0.0190-0.0025 | 0.0040-0.0325 | 0.0365-0.0075 | 0.0035-0.0300 |
| Most preferred | 0.0150-0.0040 | 0.0050-0.0250 | 0.0330-0.0090 | 0.0045-0.0150 |

The number of transitions in elements O, P, Q and R is not particularly restricted. For example, in FIG. 38, there is a transition between circumferentially adjacent longitudinal struts (R) and longitudinally adjacent circumferential rings P. However, the transition may achieved using fewer steps—e.g., by having sub-sections with constant dimensions for O, P, Q and R. In this latter embodiment, the sub-sections may be of similar or dissimilar longitudinal length. It is also possible to use a combination of one or more sub-sections with a series of individual transitions.

The embodiment of the delivery device shown in FIG. 38 preferably has a diameter less than that of delivery catheter 140,440. Preferably, the delivery device has a in the range of from about 0.015 to about 0.035 inches, more preferably from about 0.020 to about 0.030 inches, most preferably 0.025 inch.

Endovascular prosthesis delivery device 5 is particularly well suited for delivery of the present endovascular prosthesis particularly when it is desired to deliver that prosthesis through tortuous vasculature in a patient. Of course, it illustrated embodiments of the endovascular prosthesis with certain illustrated embodiments of the endovascular prosthesis delivery device with or without minor modifications to one or both of these.

In a highly preferred embodiment, the present endovascular prosthesis delivery device also is provided with a cover layer on the porous surface thereof. The cover layer may be disposed on one or both of the inner and outer surfaces of the porous surface of the endovascular prosthesis delivery device. The provision of such a cover layer has been found to obviate or mitigate friction between the endovascular prosthesis delivery device and the interior of the deliver catheter conventionally used to deliver the endovascular prosthesis. Preferably, the cover layer is a made from a biocompatible polymer which can be a natural or a synthetic polymer. Non-limiting examples of a suitable polymer may be selected from the group comprising polyurethanes, silicone materials, polyurethane/silicone combinations, rubber materials, woven and non-woven fabrics such as Dacron™, fluoropolymer compositions such as a polytetrafluoroethylene (PTFE) materials, expanded PTFE materials (ePTFE)

such as and including Teflon™, Gore-Tex™, Softform™ Impra™ and the like. Preferably, the cover layer has a thickness in the range of from about 0.00025 to about 0.00100 inches, more preferably the cover layer has a thickness of about 0.00050 inches.

The endovascular prosthesis of the present invention may further comprise a coating material thereon. The coating material can be disposed continuously or discontinuously on the surface of the prosthesis. Further, the coating may be disposed on the interior and/or the exterior surface(s) of the prosthesis. The coating material can be one or more of a biologically inert material (e.g., to reduce the thrombogenicity of the stent), a medicinal composition which leaches into the wall of the body passageway after implantation (e.g., to provide anticoagulant action, to deliver a pharmaceutical to the body passageway and the like), an expansible/swellable material (e.g., a hydrogel material) and the like.

Further, the present endovascular prosthesis may be provided with a biocompatible coating, in order of minimize adverse interaction with the walls of the body vessel and/or with the liquid, usually blood, flowing through the vessel. A number of such coatings are known in the art. The coating is preferably a polymeric material, which is generally provided by applying to the stent a solution or dispersion of preformed polymer in a solvent and removing the solvent. Non-polymeric coating material may alternatively be used. Suitable coating materials, for instance polymers, may be polytetrafluroethylene or silicone rubbers, or polyurethanes which are known to be biocompatible. Preferably however the polymer has zwitterionic pendant groups, generally ammonium phosphate ester groups, for instance phosphorylcholine groups or analogues thereof.

Examples of suitable polymers are described in International Publication Numbers WO-A-93/16479 and WO-A-93/15775. Polymers described in those documents are hemocompatible as well as generally biocompatible and, in addition, are lubricious. When such coatings are used, it is preferred that the surfaces of the endovascular prosthesis are completely coated in order to minimize unfavourable interactions, for instance with blood, which might lead to thrombosis. This good coating can be achieved by suitable selection of coating conditions, such as coating solution viscosity, coating technique and/or solvent removal step.

The manner by which the present endovascular prosthesis is manufactured is not particularly restricted. Preferably, the endovascular prosthesis is produced by laser cutting or chemical etching techniques applied to a tubular starting material. Thus, the starting material could be a thin tube of a metal or alloy (non-limiting examples include stainless steel, titanium, tantalum, nitinol, Elgiloy, NP35N, cobalt-chromium alloy and mixtures thereof) which would then have sections thereof cut out (by laser cutting or chemical etching) to provide a prosthesis having a pre-determined design. Alternatively, it is possible to cut the design (by laser cutting or chemical etching) of the prosthesis from a flat starting material and thereafter roll the cut product into a tube and heat set in such a configuration or the edges of which could be welded or otherwise secured together to form a tubular device.

In a particularly preferred embodiment, the present endovascular prosthesis is made from a suitable material which will expand when a certain temperature is reached. In this embodiment, the material may be a metal alloy (e.g., nitinol) capable of self-expansion at a temperature of at least about 25° C., preferably in the range of from about 25° C. to about 35° C. In this preferred embodiment, it may be desired and even preferable to heat set the endovascular prosthesis to adopt a deployed configuration which has been optimized for the particular intended anatomy—e.g., this is preferred for endovascular prosthesis 400,500,600 described above.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, the illustrated embodiments all utilize the leaf portion to act as a so-called flow diverter—i.e., once the device is implanted, the leaf portion diverts blood flow away from entering the aneurysmal opening. In cases where the aneurysmal opening is relatively large, it is possible to modify the leaf portion to act as a retention member—e.g., to retain one or more Guglielmi Detachable Coils in the aneurysm. In this modification, the spacing between adjacent rib portions would be increased a sufficient degree to allow delivery of one or more Guglielmi Detachable Coils through the leaf portion after implantation of the endovascular prosthesis. The Guglielmi Detachable Coils would be less likely to "fall out" of the aneurysm when the leaf portion of the present endovascular prosthesis is covering the aneurysmal opening. Further, while the illustrated embodiments depict attaching the endovascular prosthesis to the endovascular prosthesis delivery device using release wire/loop wire systems with or without male-female connection systems, other approaches may also be used—e.g., electrolytic, thermal-mechanical, other mechanical and similar approaches may be adopted. Further, while the illustrated embodiments are focussed on treatment of a cerebral aneurysm, it is contemplated that the present endovascular prosthesis may be used to treat other diseases such as aortic disease (e.g., see the discussion of aortic disease set out in International Publication Number WO 02/39924 [Erbel et al.]). In this modification, it may be appropriate to alter various of the above-mentioned dimensions. For example, It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An endovascular prosthesis comprising:
a first expandable portion expandable from a first, unexpanded state to a second, expanded state to urge the first expandable portion against a vascular lumen, the first expandable portion being disposed at a distal portion of the endovascular prosthesis and comprising a plurality of strut portions to define a first section wherein a space between adjacent strut portions is a first distance; and
a retractable leaf portion attached to the first expandable portion at a proximal portion of endovascular prosthesis, the retractable leaf portion comprising a single spine portion connected to the first expandable portion and a plurality of rib portions attached to the spine portion, the plurality of rib portions comprising a pair of rows of rib portions connected to opposed sides of the single spine portion, a combination of the single spine portion and the plurality of rib portions defining a second section wherein a space between adjacent ribs is a second distance configured to occlude an aneurysmal opening across which the retractable leaf portion is disposed, longitudinally adjacent pairs of rib portions being free of interconnecting struts wherein the first distance and the second distance are determined immediately adjacent the spine portion, and wherein the second distance is greater than the first distance.

2. The endovascular prosthesis defined in claim 1, wherein, in two dimensions, each row of rib portions is a substantial mirror image of an adjacent row of rib portions along the single spine portion.

3. The endovascular prosthesis defined in claim 1, wherein a first row of rib portions is connected at a plurality of first connection points to the single spine portion and a second row of rib portions is connected at a plurality of second connection points to the spine portion, the plurality of first connection points and the plurality of second connection points being longitudinally aligned with respect to one another.

4. The endovascular prosthesis defined in claim 1, wherein the single spine portion comprises an undulating pattern comprising alternating peaks and valleys, each rib portion being connected to a peak in the undulating pattern.

5. The endovascular prosthesis defined in claim 1, wherein a first row of rib portions is connected at a plurality of first connection points to the single spine portion and a second row of rib portions is connected at a plurality of second connection points to the single spine portion, the plurality of first connection points and the plurality of second connection points being longitudinally staggered with respect to one another.

6. The endovascular prosthesis defined in claim 1, wherein, in two dimensions, each rib portion is configured substantially to form an acute angle with respect to a spine longitudinal axis of the single spine portion.

7. The endovascular prosthesis defined in claim 1, wherein, in two dimensions, each rib portion comprises a rib proximal portion, a rib distal portion and a rib intermediate portion disposed therebetween.

8. The endovascular prosthesis defined in claim 7, wherein, in two dimensions, the rib intermediate portion has a circumferential width less than at least one of the rib proximal portion and the rib distal portion.

9. The endovascular prosthesis defined in claim 7, wherein the rib intermediate portion has a circumferential width less than both of the rib proximal portion and the rib distal portion.

10. The endovascular prosthesis defined in claim 7, wherein the rib intermediate portion comprises: (i) a rib intermediate first portion connected to the rib proximal portion and configured to form a rib intermediate first portion acute angle with respect to a longitudinal axis of the endovascular prosthesis, and (ii) a rib intermediate second portion connected to the rib distal portion and configured to form a rib intermediate second portion acute angle with respect to a longitudinal axis of the endovascular prosthesis.

11. The endovascular prosthesis defined in claim 7, wherein, in two dimensions, the rib distal portion of each rib portion is directed away from the first expandable portion.

12. The endovascular prosthesis defined in claim 1, wherein an outer region comprises the retractable leaf portion and spaces between and defined by the at least one spine portion and the plurality of rib portions of the retractable leaf portion and the outer region, in two dimensions, has an outer region area, wherein the surface areas of the at least one spine portion and the plurality of rib portions of the retractable leaf portion combine to occupy from about 15% to about 40% of said outer region area.

13. The endovascular prosthesis defined in claim 1, wherein, in two dimensions, a ratio of a perpendicular distance from a longitudinal axis to a distal tip portion of the rib portion to 50% of the circumference of the first expandable portion in the second, expanded state is in the range of from about 1:4 to about 1:1.

14. The endovascular prosthesis defined in claim 1, wherein, in two dimensions, a ratio of a perpendicular distance from a longitudinal axis to a distal tip portion of the rib portion to 50% of the circumference of the first expandable portion in the second, expanded state is in the range of from about 1:2.5 to about 1:1.5.

15. The endovascular prosthesis defined in claim 1, wherein, in two dimensions, a ratio of a perpendicular distance from a longitudinal axis to a distal tip portion of the rib portion to 50% of the circumference of the first expandable portion in the second, expanded state is about 5:9.

16. The endovascular prosthesis defined in claim 1, wherein the single spine portion is connected to the first expandable portion and a split loop portion is connected to a distal portion of the single spine portion.

17. The endovascular prosthesis defined in claim 1, further comprising a second expandable portion expandable from a first, unexpanded state to a second, expanded state to urge the first expandable portion against a vascular lumen.

18. The endovascular prosthesis defined in claim 1, wherein the prosthesis is constructed from a self-expanding material.

19. The endovascular prosthesis defined in claim 1, wherein the prosthesis is constructed from nitinol.

20. The endovascular prosthesis defined in claim 1, wherein a pair of longitudinally adjacent rib portions are spaced at a connection point to the spine portion at a distance ranging from about 0.0254 mm to about 5 mm.

21. The endovascular prosthesis defined in claim 1, wherein a pair of longitudinally adjacent rib portions are spaced at a connection point to the spine portion at a distance ranging from about 0.1400 mm to about 1 mm.

22. The endovascular prosthesis defined in claim 1, wherein a pair of longitudinally adjacent rib portions are spaced at a connection point to the spine portion at a distance ranging from about 0.1400 mm to about 0.8 mm.

23. The endovascular prosthesis defined in claim 1, wherein a pair of longitudinally adjacent rib portions are spaced at a connection point to the spine portion at a distance ranging from about 0.1400 mm to about 0.6 mm.

* * * * *